US011912645B2

(12) United States Patent
Cenac et al.

(10) Patent No.: US 11,912,645 B2
(45) Date of Patent: Feb. 27, 2024

(54) LIPOPEPTIDE COMPOUNDS FOR THE TREATMENT OF PAIN DISORDERS

(71) Applicants: INSERM (Institut National de la Santé et de la Recherche Médicale), Paris (FR); Université Paul Sabatier Toulouse III, Toulouse (FR); Centre National de la Recherche Scientifique (CNRS), Paris (FR); Centre Hospitalier Universitaire de Toulouse, Toulouse (FR); Ecole Nationale Vétérinaire de Toulouse, Toulouse (FR)

(72) Inventors: Nicolas Cenac, Toulouse (FR); Justine Bertrand-Michel, Toulouse (FR); Teresa Perez-Berezo, Toulouse (FR); Thierry Durand, Montpellier (FR); Jean-Marie Galano, Montpellier (FR); Julien Pujo, Toulouse (FR); Eric Oswald, Toulouse (FR); Patricia Martin, Toulouse (FR); Pauline Le Faouder, Toulouse (FR); Alexandre Guy, Montpellier (FR)

(73) Assignees: INSERM (INSTITUT NATIONAL DE LA SANTÉ ET DE LA RECHERCHE MÉDICALE), Paris (FR); CENTRE HOSPITALIER UNIVERSITAIRE DE TOULOUSE, Toulouse (FR); CENTRE NATIONAL DE LA RECHERCHE SCIENTIFIQUE—CNRS—, Paris (FR); ECOLE NATIONALE VETERINAIRE DE TOULOUSE, Toulouse (FR); UNIVERSITE PAUL SABATIER TOULOUSE III, Toulouse (FR); INSTITUT NATIONAL DE RECHERCHE POUR L'AGRICULTURE, L'ALIMENTATION ET L'ENVIRONNEMENT, Paris (FR); UNIVERSITE DE MONTPELLIER, Montpellier (FR); ECOLE NATIONALE SUPERIEURE DE CHIMIE DE MONTPELLIER, Montpellier (FR)

( * ) Notice: Subject to any disclaimer, the term of this patent is extended or adjusted under 35 U.S.C. 154(b) by 306 days.

(21) Appl. No.: 16/607,772

(22) PCT Filed: Apr. 27, 2018

(86) PCT No.: PCT/EP2018/060873
§ 371 (c)(1),
(2) Date: Oct. 24, 2019

(87) PCT Pub. No.: WO2018/197666
PCT Pub. Date: Nov. 1, 2018

(65) Prior Publication Data
US 2020/0048187 A1    Feb. 13, 2020

(30) Foreign Application Priority Data

Apr. 28, 2017 (EP) ..................................... 17305481

(51) Int. Cl.
*C07C 233/47* (2006.01)
*A61P 29/00* (2006.01)

(52) U.S. Cl.
CPC ............ *C07C 233/47* (2013.01); *A61P 29/00* (2018.01)

(58) Field of Classification Search
CPC ...... C07C 45/50; C07C 29/141; C07C 29/149
USPC ......................................................... 514/626
See application file for complete search history.

(56) References Cited

FOREIGN PATENT DOCUMENTS

WO    2010/109284 A1    9/2010

OTHER PUBLICATIONS

Meena et al.; "Lipopeptides as the Antifungal and Antibacterial Agents: Applications in Food Safety and Therapeutics"; Biomed Research International, vol. 2015, Jan. 1, 2015, pp. 1-9.

*Primary Examiner* — Ana Z Muresan
(74) *Attorney, Agent, or Firm* — WC&F IP

(57) ABSTRACT

The invention is based on the discovery of a new bacterial compound with analgesic properties which could be used as a new tool for the treatment of pain disorders such as visceral pain. Studying the mechanisms implicated in analgesic properties of the probiotic *Escherichia coli* strain Nissle 1917 (EcN), inventors characterized, the amino fatty acids produced by EcN, which display the Ecn analgesic properties. One of these compounds inhibits the hypersensitivity to colorectal distension induced by capsaicin, which is a very powerful nociceptive compound and acts via the GABA B receptor. Furthermore, inventors demonstrate that this compound is able to cross the cellular epithelial barrier (such as the intestinal epithelium). Thus, the invention relates to a lipopetide compound, derived from gamma-aminobutyric acid. The invention also relates to a lipopeptide compound according to the invention for the treatment of treating pain disorder, such as somatic pain and visceral pain.

9 Claims, 18 Drawing Sheets

Figure 3A:
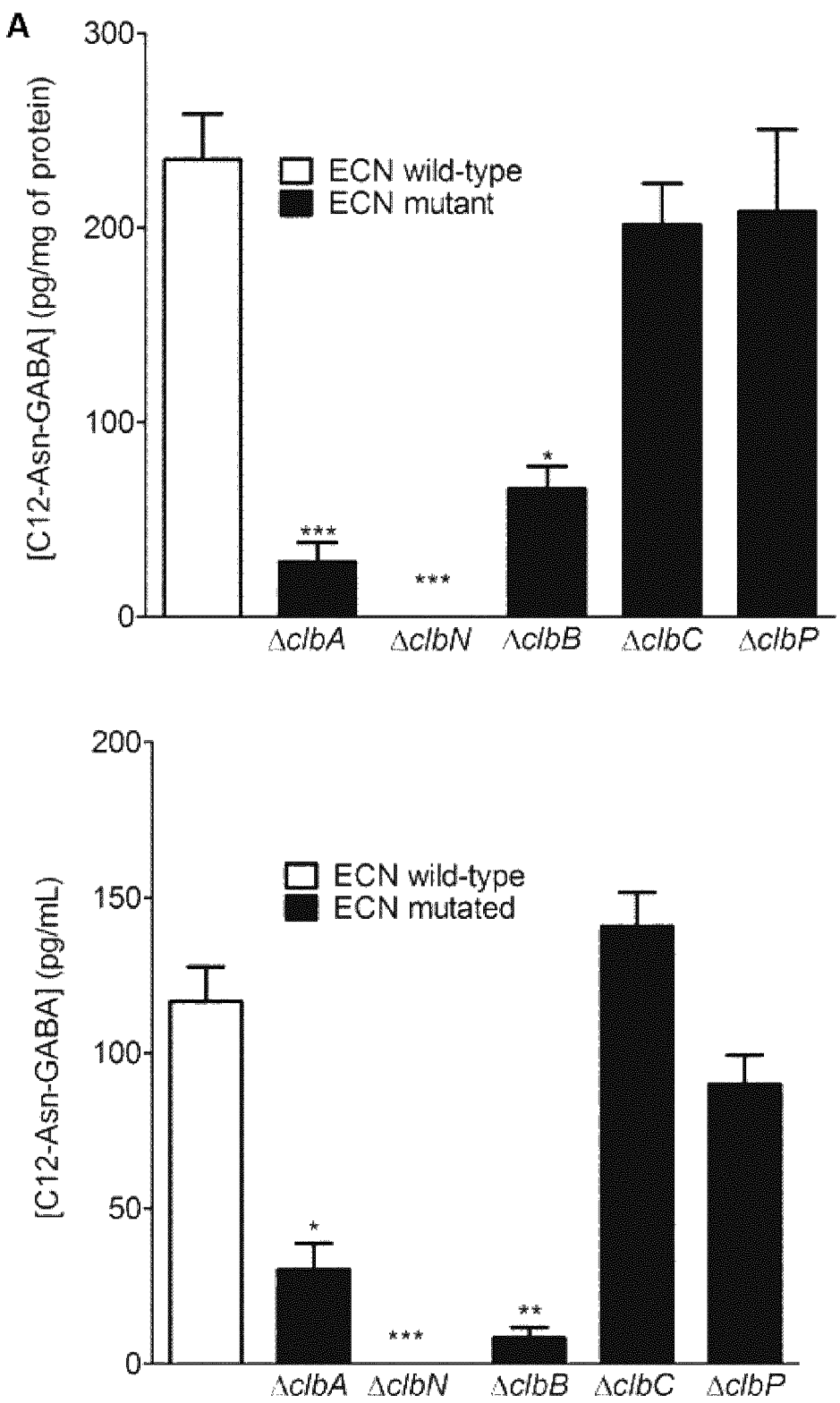

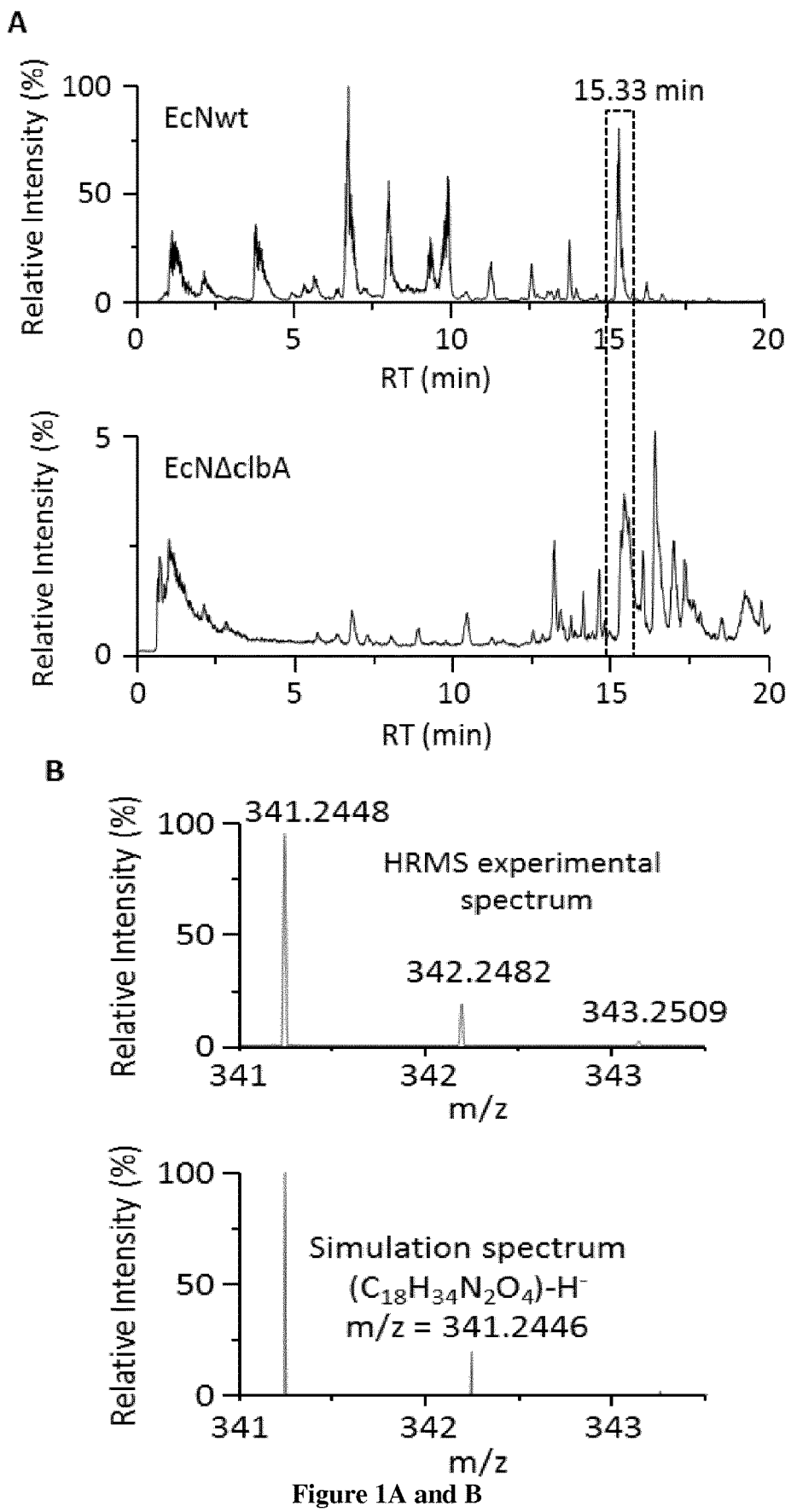
Figure 1A and B

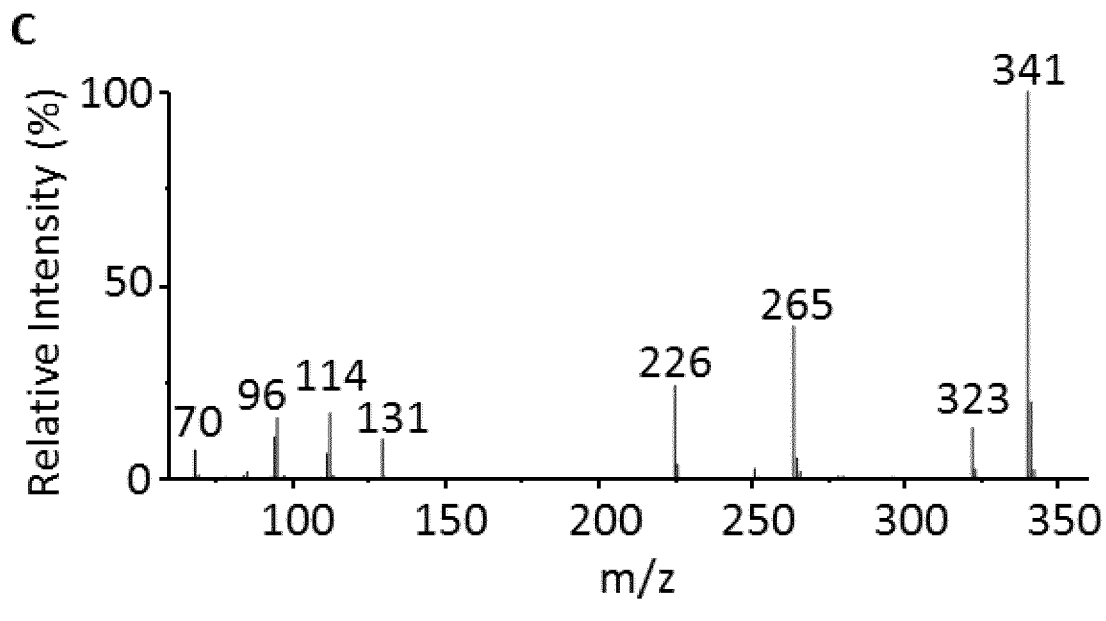
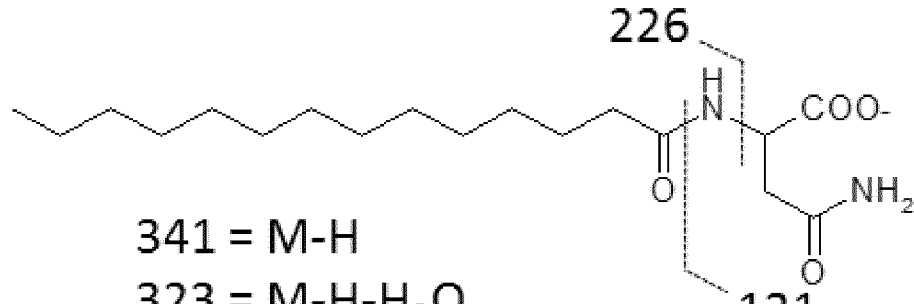
341 = M-H
323 = M-H-H$_2$O
226 = RCONH-H
131 = Asn-H
114 = Asn-H-NH$_3$
96 = Asn-H-NH$_3$-H$_2$O
Figure 1 C

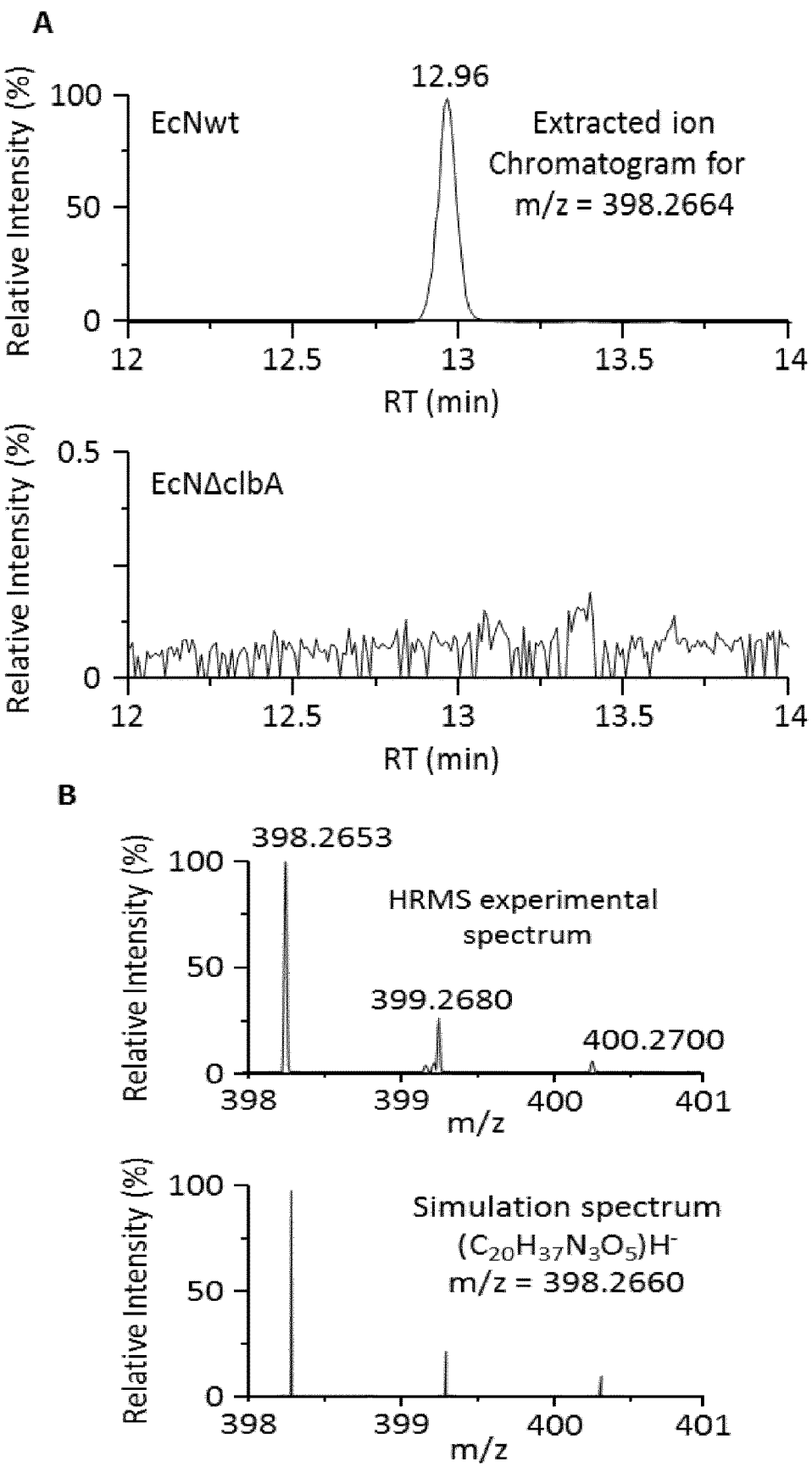
Figure 2 A and B

C
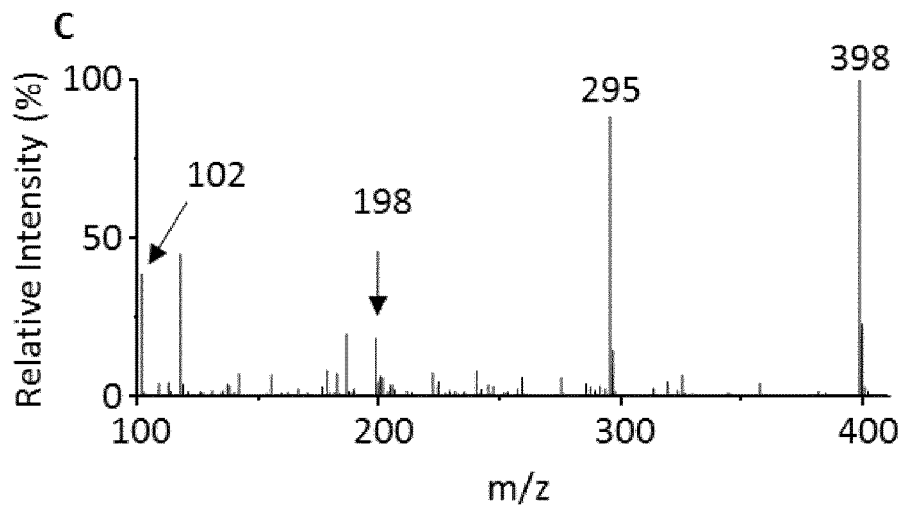
398 = M-H
295 = M-aminobutyric acid-H
198 = RCONH-H
102 = aminobutyric acid-H
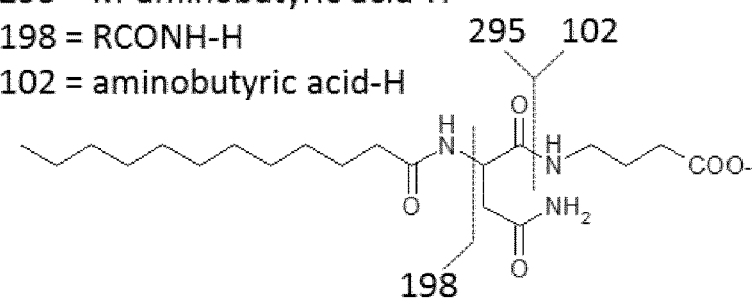
D
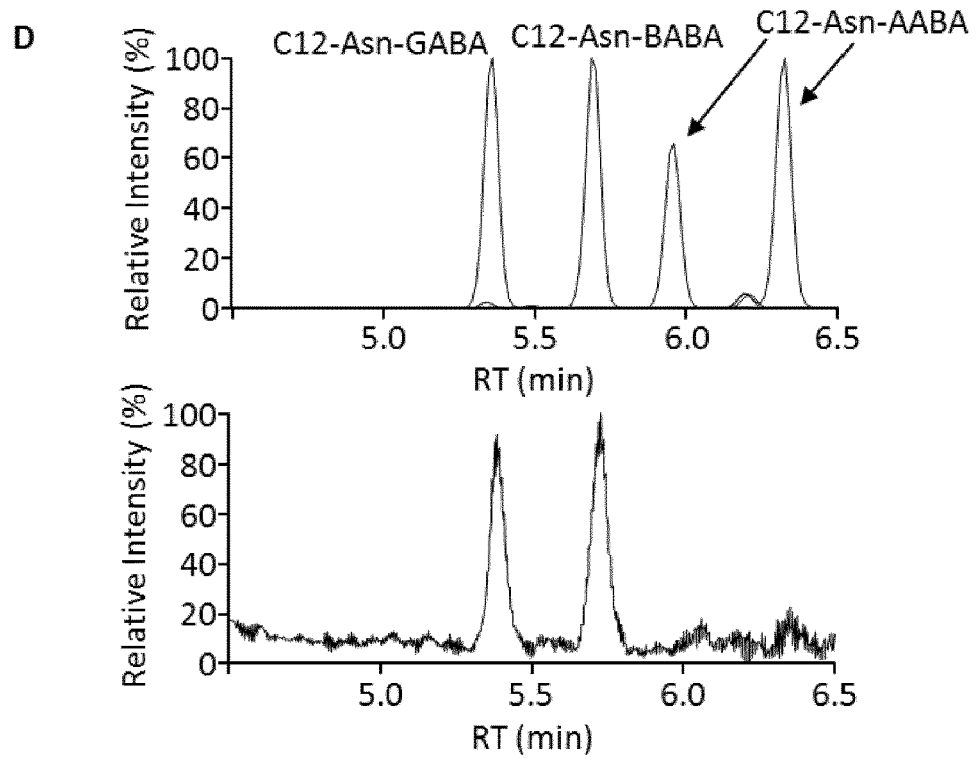
Figure 2 C and D

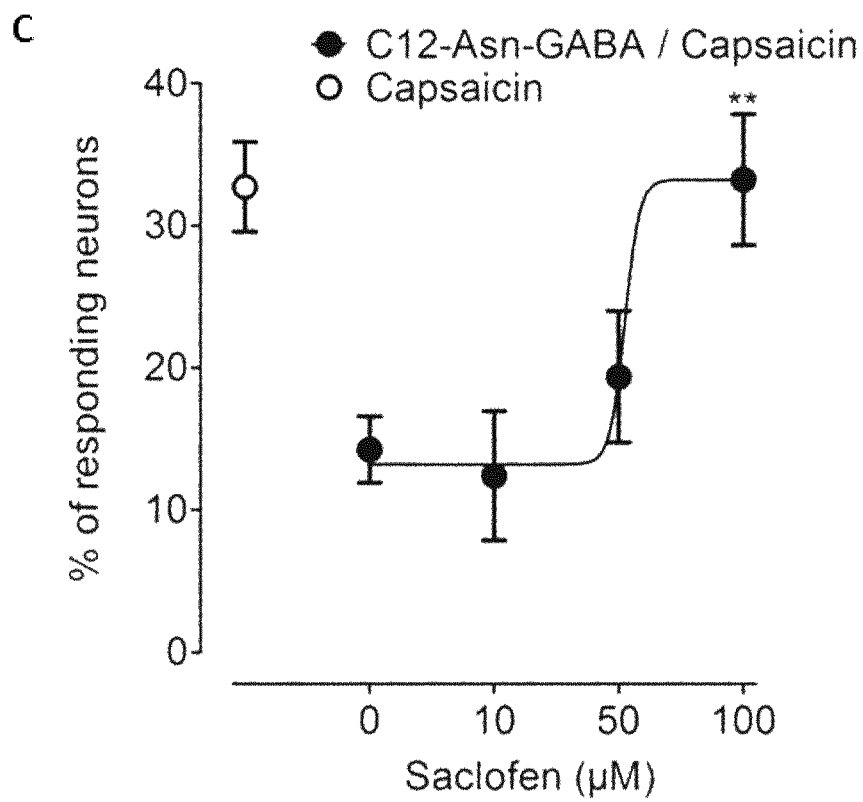
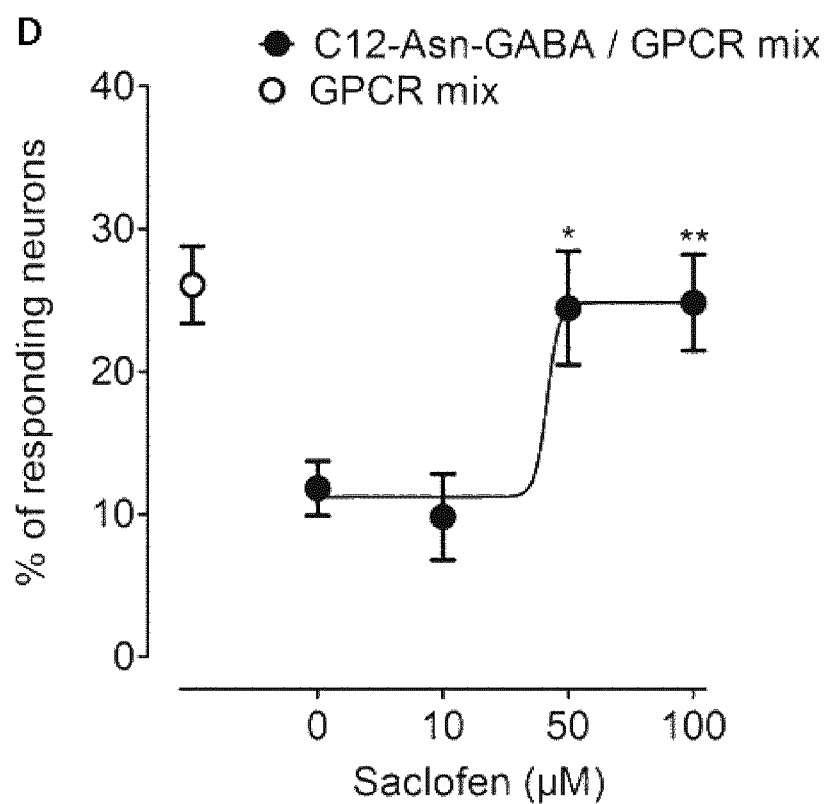
Figure 4C and D

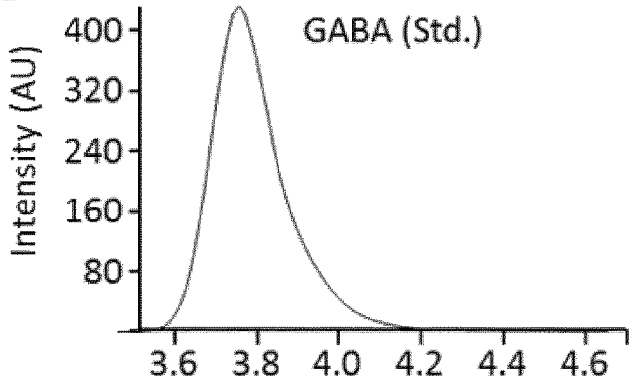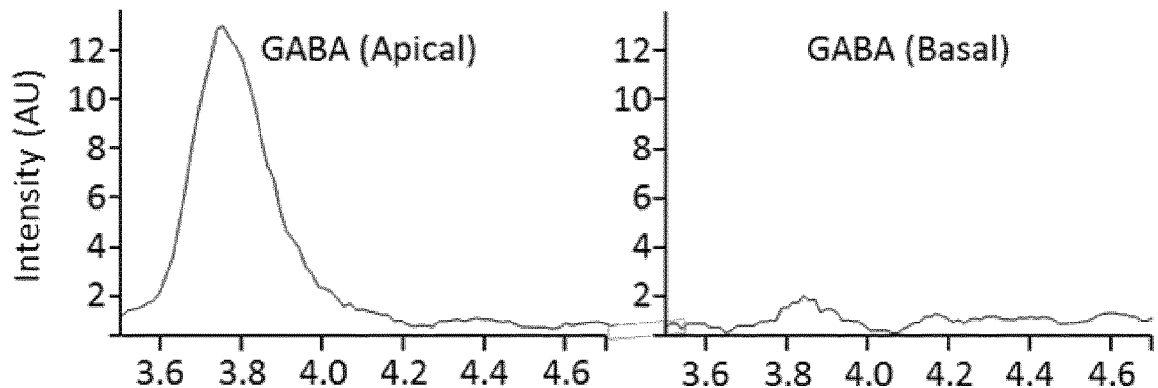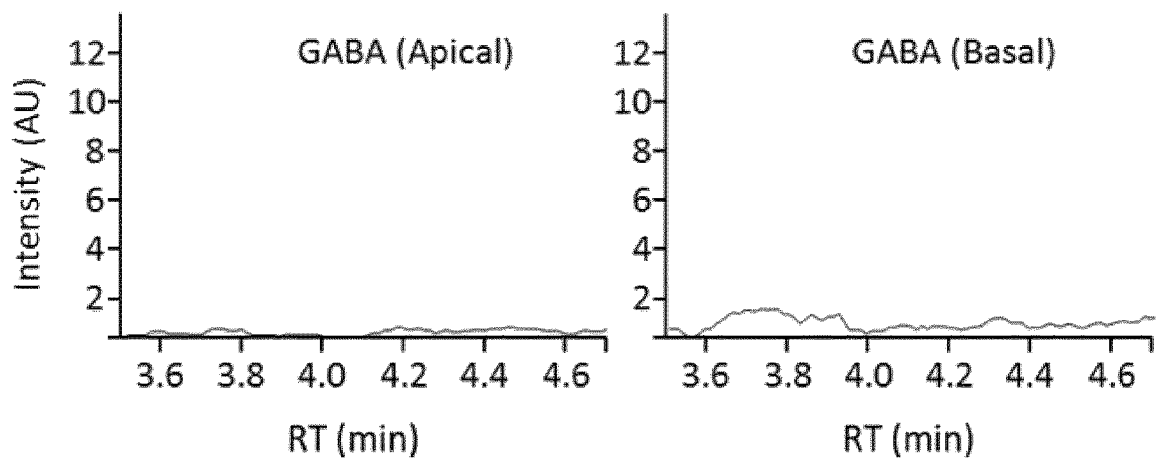
Figure 5B

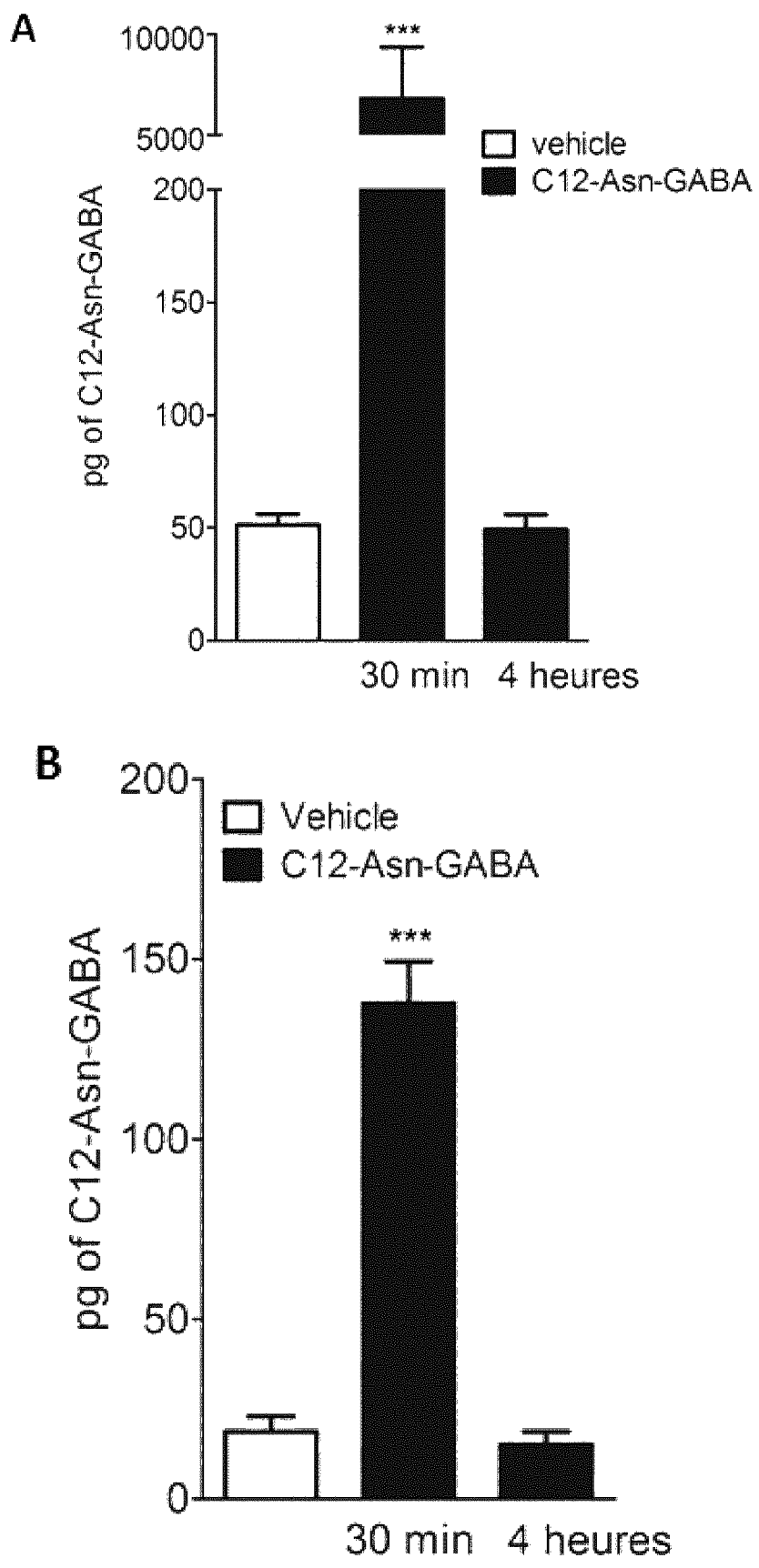
Figure 6A and B

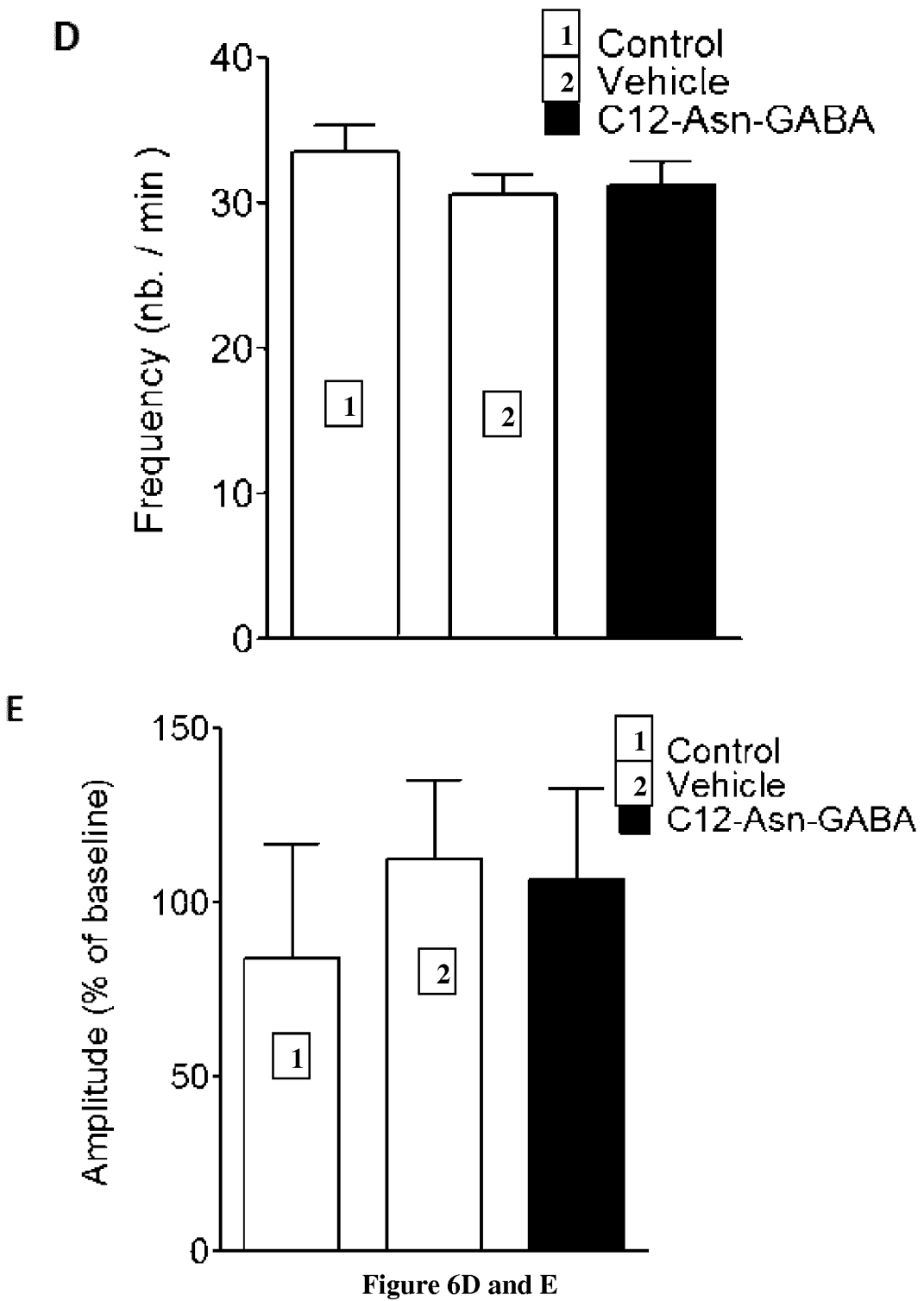
Figure 6D and E

LIPOPEPTIDE COMPOUNDS FOR THE TREATMENT OF PAIN DISORDERS

FIELD OF THE INVENTION

The invention relates to a lipopeptide compound and their use for treating pain disorders. In particular, the invention concerns novel lipopetide compound, including without limitation, a compound with C12-Asn-GABA structure their derivatives and their uses, for treating visceral pain and somatic pain.

BACKGROUND OF THE INVENTION

Pain is an unpleasant feeling often caused by intense or damaging stimuli. The International Association for the Study of Pain's widely used definition states: "Pain is an unpleasant sensory and emotional experience associated with actual or potential tissue damage, or described in terms of such damage". For example, chronic pain is a common problem that constitutes a major challenge to healthcare providers because of its complex natural history, unclear etiology, and poor response to therapy. Chronic pain is a poorly defined condition. Most authors consider ongoing pain lasting longer than 6 months as diagnostic, whereas others have used 3 months as the minimum criterion. In chronic pain, the duration parameter is used arbitrarily. Some authors suggest that any pain that persists longer than the reasonable expected healing time for the involved tissues should be considered chronic pain. The pathophysiology of chronic pain is multifactorial and complex and is still poorly understood. Various neuromuscular, reproductive, gastrointestinal, and urologic disorders may cause or contribute to chronic pain.

Irritable bowel syndrome (IBS) is a functional gastrointestinal (GI) disorder characterized by recurrent episodes of abdominal pain/discomfort and bowel habit changes (e.g. constipation, diarrhea)[1]. With a global prevalence of ~11%[1], IBS constitutes one of the most common conditions leading to gastroenterological referral, and results in a considerable disease burden. While the pathophysiology of IBS is not fully understood, visceral hypersensitivity (VH; enhanced sensitivity of the intestinal wall to local stimuli) has been proposed as a key mechanism underlying abdominal pain, one of the most debilitating and most troublesome symptoms of this disorder[2-4]. Current treatments for IBS are mainly symptoms orientated; however, the overall efficacy is low and there are no drugs specifically approved for abdominal pain[5]. Thus, selective pharmacological tools targeting VH may be considered a suitable therapeutic approach for visceral pain treatment and development of novel IBS therapies.

Data from clinical research suggest that certain probiotic bacterial strains have the potential to modulate abdominal pain in IBS[6-9]. Nonetheless, this data differs considerably among studies due to the probiotic bacterial strains used for the treatment and the heterogeneity of IBS groups included. Moreover, the mechanisms of action responsible for the claimed therapeutic effects differ from one strain to another.

*Escherichia coli* Nissle 1917 (EcN) is the active component of Mutaflor® (Ardeypharm GmbH, Herdecke, Germany), a probiotic drug licensed in several countries for the treatment of multiple intestinal disorders[10]. Clinical trials have shown EcN to be effective for the treatment of abdominal pain in IBS patients[11,12] but very little is known about the specific mechanisms through which EcN exerts the ascribed analgesic effects. EcN is known to harbor a genomic island, named pks, which carries a cluster of genes that enables the synthesis of hybrid peptide polyketides and especially a genotoxin called colibactin (fig. S1)[13]. Colibactin is a structurally uncharacterized PK-NRP that is thought to arise from a pro-drug called precolibactin, which has also not been fully structurally elucidated[14,15]. This toxin is produced by a complex biosynthetic machinery involving the sequential action of proteins ClbA to ClbS[16]. The core machinery consists of three polyketide synthases, three non-ribosomal peptide synthetases and two hybrids PKS-NRPS[16]. The machinery also employs additional maturation proteins and efflux pump(s). ClbA a phosphopantetheinyl transferase (PPTase) essential for the activation of the NRPS and PKS enzymes[16]. ClbA is mandatory for the biosynthesis of colibactin[13] but is also involved in the biosynthesis of other bioactive metabolites such as the siderophores enterobactin, salmochelin and yersiniabactin[17]. Following activation by ClbA, the initiating NRPS ClbN uses Asn as a substrate to generate an N-myristoyl-D-Asn. The NRPS-PKS assembly line continues the synthesis of precolibactin compound(s) using malonyl-coA and different amino acids[18-20] as substrates. The precolibactin is then cleaved by peptidase ClbP to liberate colibactin and N-myristoyl-D-Asn (C14-Asn, fig. S1)[18,21,22].

Surprisingly, although colibactin was shown to be a bona fide virulence factor and a putative carcinogenic agent[13], this genotoxin is also produced by EcN. The probiotic activity of EcN can apparently not be dissociated from its genotoxic activity, since inactivation of clbA required for the activation of the NRPS and PKS enzymes leading to colibactin production also attenuates the probiotic activity of EcN in experimental colitis[23]. A possible explanation for the dual role of colibactin in EcN may be that that the pks island code for additional bioactive compounds distinct from colibactin and involved in the probiotic activity[16,24]. This hypothesis has been recently reinforced by the structural characterization of several colibactin pathway-dependent small molecules[14,15,22]. Hence, the identification and functional characterization of new molecules derived from the colibactin encoding hybrid PKS-NRPS biosynthetic gene clusters may help to decipher some of the mechanisms supporting the capacity of EcN to modulate abdominal pain and thereby, allowing the design of novel analgesic agents devoid of genotoxic properties. Here, it is described an interdisciplinary work that has led to the isolation and structural elucidation of a new metabolite encoded by the pks island that shows potent anti-nociceptive properties in vitro and in vivo. While an increased number of small molecules derived from the colibactin encoding hybrid PKS-NRPS biosynthetic gene clusters have been described[18,19,22], this is the first study characterizing a non-genotoxic bioactive metabolite in vivo. This analgesic compound produced by probiotic bacteria may represent a promising therapeutic agent in somatic pain and visceral pain.

SUMMARY OF THE INVENTION

The invention is based on the discovery of a new bacterial compound with analgesic properties that could be used as a new tool for the treatment of pain disorders such as visceral pain (i.e. IBS). The study of the mechanisms implicated in the analgesic properties of the probiotic *Escherichia coli* strain Nissle 1917 (EcN) has allowed the inventors to characterize, by chromatography coupled with high resolution mass spectrometry and genetic studies, an amino fatty acid with potential analgesic properties. This compound is capable of inhibiting the hypersensitivity to colorectal distension induced by capsaicin, which is a powerful nociceptive compound, and acts via the GABA B receptor.

Furthermore, inventors have demonstrated that this compound is able to cross a monolayer of human intestinal epithelial cells in vitro and mouse colon in vivo. In contrast, GABA alone was not able to cross the epithelium. In naive mouse, this compound is quantified in all tested compartments (central nervous system, blood and periphery). Based on its capacity to cross epithelial and blood-brain barriers, inventors consider that this compound could be used for somatic pain with a direct application on skin.

Thus, the invention relates to a lipopeptide compound derived from gamma-aminobutyric acid of formula I (see below).

The invention also relates to a lipopeptide compound according to the invention for use in the treatment of pain disorder, such as somatic pain and visceral pain.

A further object of the invention relates to a therapeutic composition comprising lipopeptide compound, as defined above.

Finally, a method to synthesize the lipopeptide compound is also described.

DETAILED DESCRIPTION OF THE INVENTION

Lipopetide Compound

In a first aspect, the present invention provides a compound having the following structure of formula (I):

RC(O)—Xaa-Xbb-Y     (I), wherein
R is a C5-C19 (fatty) hydrocarbon chain,
Xaa is an asparagine or an equivalent polar and non-charged amino acid selected from the list consisting of serine, threonine or glutamine moiety,
Xbb is a gamma-aminobutyric acid moiety,
Y is —OH or NH2,
or a pharmaceutical acceptable salt thereof.

Structurally, cell membranes constitute a complex set of lipids, proteins and sugars (or oses) organized on the basis of a double phospholipid sheet. Thus, cell membranes act as real physicochemical barriers through the regulation of the cellular matter exchange. For instance, GABA alone is not able to cross cell membrane. The ability of the compound of the invention to cross the cellular epithelial barrier is linked to the (fatty) hydrocarbon chain of the compound which must contain at least 5 carbons to cross membrane cells.

The term "C5-C19 (fatty) hydrocarbon chain" group means a saturated or unsaturated hydrocarbon chain, linear or branched, comprising from 5 to 19 carbon atoms, such as for example an alkyl, alkene or alkyne, etc.

In one embodiment, R is selected from the list consisting of alkyl, alkene or alkyne.

In a specific embodiment, R is a C5-C19 alkyl. In a more specific embodiment R is a C11 alkyl.

"C5-C19 alkyl" group means a saturated hydrocarbon chain, linear or branched, comprising from 1 to 19 carbon atoms.

In a specific embodiment, C5-C19 alkyl of the compound according to the present invention has the following structure:

CH3-CyHx-, where y=4 to 18, x=2y. In a specific embodiments, y=8 to 14. For example, y=10.

The term gamma-Aminobutyric acid (γ-Aminobutyric acid) (also called GABA) means the chief inhibitory neurotransmitter in the mammalian central nervous system. It plays the principal role in reducing neuronal excitability throughout the nervous system (see Watanabe M, et al (2002). "GABA and GABA receptors in the central nervous system and other organs". Int. Rev. Cytol. 213. p. 1-47). Although in chemical terms it is an amino acid (as it has both a primary amine and a carboxylic acid functional group), GABA is rarely referred to as such in the scientific or medical community. By convention the term "amino acid", when used without a qualifier, refers specifically to an alpha amino acid. GABA is not an alpha amino acid, meaning the amino group is not attached to the alpha carbon so it is not incorporated into proteins.

Gamma-Aminobutyric acid Formula is

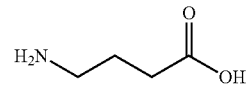

The GABA moiety is preferably linked to asparagine (or equivalent polar and non-charged amino acid of asparagine) through its amine functional group.

In a specific embodiment, Y is OH—.

In one embodiment Xaa is asparagine

In another embodiment Xaa is equivalent polar and non-charged amino acid of asparagine selected from the group consisting of serine, threonine and glutamine.

In the preferred embodiment, for the compound of formula (I), the RC(O) group is at the N terminal side of the lipopeptide and the GABA moiety is a C terminal side of the lipopeptide.

As used herein, the term "amino acid" refers to natural or unnatural amino acids in their D and L stereoisomers for chiral amino acids. It is understood to refer to both amino acids and the corresponding amino acid residues, such as are present, for example, in peptidyl structure. Natural and unnatural amino acids are well known in the art. Common natural amino acids include, without limitation, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr), and valine (Val). Uncommon and unnatural amino acids include, without limitation, allyl glycine (AllylGly), norleucine, norvaline (Avl), biphenylalanine (Bip), citrulline (Cit), 4-guanidinophenylalanine (Phe(Gu)), homoarginine (hArg), homolysine (hLys), 2-naphtylalanine (2-Nal), ornithine (Orn) and pentafluorophenylalanine.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Amino acids may further be classified as non-charged, or charged (positively or negatively) amino acids. Examples of positively charged amino acids include without limitation lysine, arginine and histidine. Examples of negatively charged amino acids include without limitation glutamic acid and aspartic acid. Additional amino acids that are classified in each of the above groups are known to those of ordinary skill in the art.

"Equivalent amino acid" means an amino acid which may be substituted for another amino acid in the peptide compounds according to the invention without any appreciable loss of function. Equivalent amino acids will be recognized by those of ordinary skill in the art. Substitution of like amino acids is made on the basis of relative similarity of side chain substituents, for example regarding size, charge, hydrophilicity and hydrophobicity as described herein. The phrase "or an equivalent amino acid thereof" when used following a list of individual amino acids means an equivalent of one or more of the individual amino acids included in the list.

In a particular embodiment, the compound of the invention consists of

C11 C(O)-Asn-gamma-aminobutyric acid

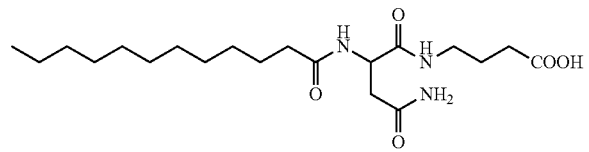 [SMILES: CCCCCCCCCCCC(=O)NC(CC(N)=O)C(=O)NCCCC(=O)O]

The compound of the invention may be obtained by direct purification from any bacterium containing the pks island—preferably from *Escherichia coli* Nissle 1917 (EcN)-, or by any one of synthetic chemical method which is well known from the one skilled in the art.

For example, the lipopeptide compounds of interest may be recovered from either the culture medium or the bacterium cell lysates. Typically, the lipopeptide compounds of the invention are isolated from *Escherichia coli*. For example the lipopeptide compound of the invention may be isolated from *Escherichia coli* Nissle 1917 (EcN). Bacteria employed in production of the lipopetides of interest can be disrupted by various physical or chemical means, such as freeze-thaw cycling, sonication, mechanical disruption, or cell-lysing agents.

Purification of the lipopeptide of interest from bacteria may be preferred. The procedures described in the Example are exemplary of suitable procedures for purification of lipopeptide compounds from the supernatant of *Escherichia coli* Nissle 1917 (EcN) (or any bacteria containing pks island or containing at least enzymes encoding by ClbA, ClbN and ClbB)).

The following procedures are exemplary of suitable purification procedures of lipopeptide compound: include: lipopeptide fractionation with spectrometry coupled on-line to a liquid chromatography (as used in the example); reverse phase HPLC; chromatography on silica or on a cation-exchange resin such as DEAE; chromatofocusing; SDS-PAGE; ammonium sulfate precipitation; gel filtration using, for example, Sephadex G-75; Protein A Sepharose columns to remove contaminants; and metal chelating columns to bind epitope-tagged forms of the lipopeptide of interest.

The purification step(s) selected will depend on the nature of the production process used and the particular lipopeptide compound produced.

The protocol for the production of the lipopeptide compound, by means of bacteria culture is also described in "Screening concepts, characterization and structural analysis of microbial-derived bioactive lipopeptides: a review." Crit Rev Biotechnol. 2017 May; 37(3):393-410. doi: 10.3109/07388551.2016.1163324.

In certain embodiments, the lipopeptide compound of the invention may be synthesised through conventional techniques of chemical synthesis.

Method for Treating Pain Disorder

Accordingly a first object of the present invention relates to a method of treating pain in a subject thereof, the method comprising administering the subject a therapeutically effective amount of compound of the invention.

Treatment may be for any purpose, including the therapeutic treatment of subjects suffering from pain, as well as the prophylactic treatment of subjects who do not suffer from pain (e.g., subjects identified as being at high risk pain). As used herein, the terms "treatment," "treat," and "treating" refer to reversing, alleviating, inhibiting the progress of a disease or disorder as described herein (i.e. pain), or delaying, eliminating or reducing the incidence or onset of a disorder or disease as described herein, as compared to that which would occur in the absence of the measure taken. The terms "prophylaxis" or "prophylactic use" and "prophylactic treatment" as used herein, refer to any medical or public health procedure whose purpose is to prevent the disease herein disclosed (i.e. pain). As used herein, the terms "prevent", "prevention" and "preventing" refer to the reduction in the risk of acquiring or developing a given condition (i.e. pain), or the reduction or inhibition of the recurrence or said condition (i.e. pain) in a subject who is not ill, but who has been or may be near a subject with the condition (i.e. pain).

The method of the present invention is suitable in the treatment of a wide range of pain disorders, particularly acute pain, chronic pain, neuropathic pain, inflammatory pain, iatrogenic pain—including cancer pain, infectious pain including herpetic pain visceral pain-, central pain, disorders of pain dysfunction including fibromyalgia, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

Pain is generally classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain. Clinical pain is present when discomfort and abnormal sensitivity feature among the patient's symptoms. Patients tend to be quite heterogeneous and may display various pain symptoms. Such symptoms include: 1) spontaneous pain which may be dull, burning, or stabbing; 2) exaggerated pain responses to noxious stimuli (hyperalgesia); and 3) pain produced by normally innocuous stimuli. Although patients suffering from various forms of acute and chronic pain may have similar symptoms, the underlying mechanisms may be different and may, therefore, require different treatment strategies. Pain can also be divided into a number of different subtypes according to the pathophysiology, including nociceptive, neuropathic and inflammatory pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, postoperative pain (pain following any type of surgical procedure), posttraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

There are two types of nociceptive pain: "somatic" pain and "visceral" pain.

"Somatic" pain is caused by injury to skin, muscles, bone, joint, and connective tissues. Deep somatic pain is usually described as dull or aching, and localized in one area. Somatic pain from injury to the skin or the tissues just below it often is sharper and may have a burning or pricking quality. Generally, "Somatic" pain is well-localized pain that results from the activation of peripheral nociceptors without injury to the peripheral nerve or central nervous system.

Somatic pain often involves inflammation of injured tissue. Although inflammation is a normal response of the body to injury, and is essential for healing, inflammation that does not disappear with time can result in a chronically painful disease. The joint pain caused by rheumatoid arthritis may be considered an example of this type of somatic nociceptive pain.

"Visceral" pain refers to pain that originates from ongoing injury to the internal organs or the tissues that support them. When the injured tissue is a hollow structure, like the intestine or the gall bladder, the pain often is poorly localized and cramping. When the injured structure is not a hollow organ, the pain may be pressure-like, deep, and stabbing. Visceral pain could also be associated with a subtype of inflammation (see below)

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 0.36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders inducing pain include functional bowel disorder (FBD) and inflammatory bowel disease (IBD). These GI disorders include a wide range of disease states that are currently only moderately controlled including in respect of FBD-, gastro-esophageal reflux, dyspepsia, irritable bowel syndrome (IBS) and functional abdominal pain syndrome (FAPS) and -in respect of IBD-Crohn's disease, ileitis and ulcerative colitis, all of which regularly produce visceral pain. Other types of visceral pain include the pain associated with dysmenorrhea, cystitis and pancreatitis and pelvic pain.

In some embodiments the method of the present invention is particularly suitable for the treatment of visceral pain resulting from gastrointestinal disorders, including functional bowel disorder (FBD) and inflammatory bowel disease (IBD) gastro-esophageal reflux, dyspepsia, irritable bowel syndrome (IBS) and functional abdominal pain syndrome (FAPS), and, in respect of IBD, Crohn's disease, ileitis, ulcerative colitis dysmenorrhea, cystitis and pancreatitis and pelvic pain.

In a specific embodiment, visceral pain is selected from the group consisting of Inflammatory Bowel Diseases (IBD) or Irritable Bowel Syndrome (IBS).

As used herein, the term "Irritable Bowel Syndrome (IBS)" is a term for a variety of pathological conditions causing discomfort in the gastro-intestinal tract. It is a functional bowel disorder characterized by chronic abdominal pain, discomfort, bloating, and alteration of bowel habits in the absence of any organic cause. It also includes some forms of food-related visceral hypersensitivity, such as Gluten hypersensitivity (ie. Celiac disease).

As used herein, the term "inflammatory bowel diseases (IBD)" is a group of inflammatory diseases of the colon and small intestine. The major types of IBD are Crohn's disease, ulcerative colitis and pouchitis.

In some embodiments, the method of the present invention is suitable for the treatment of somatic pain caused by injury to skin, muscles, bone, joint, and connective tissues, such as superficial pain (from the skin or subcutaneous tissue) and deep pain (from deeper structures of the body wall).

In some embodiments, the method of the present invention is particularly suitable for the treatment of chronic pain which results from musculoskeletal disorders such as osteoarthritis/degenerative joint disease/spondylosis, rheumatoid arthritis, lyme disease, reiter syndrome, disk herniation/facet osteoarthropathy, fractures/compression fracture of lumbar vertebrae, faulty or poor posture, fibromyalgia, polymyalgia rheumatica, mechanical low back pain, chronic coccygeal pain, muscular strains and sprains, pelvic floor myalgia (levator ani spasm), piriformis syndrome, rectus tendon strain, hernias (e.g. obturator, sciatic, inguinal, femoral, spigelian, perineal, umbilical), abdominal wall myofascial pain (trigger points), chronic overuse syndromes (e.g., tendinitis, bursitis); neurological disorders such as, brachial plexus traction injury, cervical radiculopathy, thoracic outlet syndrome, spinal stenosis, arachnoiditis syndrome, metabolic deficiency myalgias, polymyositis, neoplasia of spinal cord or sacral nerve, cutaneous nerve entrapment in surgical scar, postherpetic neuralgia (shingles), neuralgia (e.g., iliohypogastric, ilioinguinal, or genitofemoral nerves), polyneuropathies, polyradiculoneuropathies, mononeuritis multiplex, chronic daily headaches, muscle tension headaches, migraine headaches, temporomandibular joint dysfunction, temporalis tendonitis, sinusitis, atypical facial pain, trigeminal neuralgia, glossopharyngeal neuralgia, nervus intermedius neuralgia, sphenopalatine neuralgia, referred dental or temporomandibular joint pain, abdominal epilepsy, abdominal migraine, urologic disorders, bladder neoplasm, chronic urinary tract infection, interstitial cystitis, radiation cystitis, recurrent cystitis, recurrent urethritis, urolithiasis, uninhibited bladder contractions (detrusor-sphincter dyssynergia), urethral diverticulum, chronic urethral syndrome, urethral carbuncle, prostatitis, urethral stricture, testicular torsion, peyronie disease; gastrointestinal disorders such as chronic visceral pain syndrome, gastroesophageal reflux, peptic ulcer disease, pancreatitis, chronic intermittent bowel obstruction, colitis, chronic constipation, diverticular disease, inflammatory bowel disease, irritable bowel syndrome; reproductive disorders (extrauterine) such as endometriosis, adhesions, adnexal cysts, chronic ectopic pregnancy, chlamydial endometritis or salpingitis, endosalpingiosis, ovarian retention syndrome (residual ovary syndrome), ovarian remnant syndrome, ovarian dystrophy or ovulatory pain, pelvic congestion syndrome, postoperative peritoneal cysts, residual accessory ovary, subacute salpingo-oophoritis, tuberculous salpingitis; reproductive disorders (uterine) such as adenomyosis, chronic endometritis, atypical dysmenorrhea or ovulatory pain, cervical stenosis, endometrial or cervical polyps, leiomyomata, symptomatic pelvic relaxation (genital prolapse), intrauterine contraceptive device; psychological disorders such as bipolar personality disorders, depression, porphyria, sleep disturbances; and other conditions such as cardiovascular disease (eg, angina), peripheral vascular disease and chemotherapeutic, radiation, or surgical complications.

In some embodiments the method of the present invention is suitable for the treatment of pain which results from autoimmune diseases including multiple sclerosis, neurodegenerative disorders, neurological disorders including epilepsy and senso-motor pathologies, osteoarthritis, rheumatoid arthritis, neuropathological disorders, pain associated with dysmenorrhea, pelvic pain, cystitis, pancreatitis, migraine, cluster and tension headaches, diabetic neuropathy, peripheral neuropathic pain, sciatica, causalgia, and conditions of lower urinary tract dysfunction.

In some embodiments, the prophylactic methods of the invention are particularly suitable for subjects who are identified as at high risk for pain. Typically subject that are risk for pain include patient that will have a surgical operation.

Said compound of the present invention can be used as a drug, in particular as analgesic. The compounds are useful for example in the treatment of pain disorders such as chronic pain and visceral pain.

The skilled man in the art can easily evaluate the analgesic properties of the amino lipid compound of the invention by assessing the capacity of said compound to inhibit neuronal activation of sensory nerves via the $GABA_B$ receptor by means of calcium signaling studies in sensory neurons. The analgesic properties may be also tested by neuronal electrophysiology in vitro, axonal recording ex vivo, using animal model of pain (see N Gregory, A L Harris, C R Robinson, P M Dougherty, P N Fuchs, and K A Sluka. An overview of animal models of pain: disease models and outcome measures. J Pain. 2013 November; 14(11)). Typically, the tests that may be used to assess the analgesic activity of a lipopeptide compound are described in the Examples (FIG. 4 and FIG. 6). In a second step, the ability to cross the epithelial barrier can also be tested in vitro in a transwell system, in vivo by a direct quantification of the lipolipide in different organs (see the test described in Example and FIGS. 5 and 6) or ex vivo by the use of using chamber (see H. J. Galipeau & E. F. Verdu. The complex task of measuring intestinal permeability in basic and clinical science. Neurogastroenterol Motil (2016) 28, 957-965).

It will be understood that the daily dose of the compounds and the composition of the present invention will be decided by the attending physician within the scope of sound medical judgment. The specific therapeutically effective dose for any particular patient will depend upon a variety of factors including the type and severity of the disorder to treat; activity of the specific compound employed; the specific composition employed, the age, body weight, general health, sex and diet of the patient; the time and route of administration and the rate of excretion of the specific compound employed; the duration of the treatment; drugs used in combination or coincidental with the specific lipopeptide employed and other factors well known in the medical arts. For example, within the skill of the art it is recommended to start the treatment with doses of the compound at levels lower than those required to achieve the desired therapeutic effect and to gradually increase the dosage until the desired effect is achieved.

The compound of the invention may be administered by any suitable route of administration. For example, the compound according to the invention it can be administered by oral (including buccal and sublingual), rectal, nasal, topical, pulmonary, vaginal, or parenteral (including intramuscular, intra-arterial, intrathecal, subcutaneous and intravenous).

In a preferred embodiment of the invention, the therapeutic composition containing the compound of the invention is administered intrarectally, topically or orally. A rectal administration preferably takes place in the form of a suppository, enema or foam. Intrarectal administration is particularly suitable for intestinal diseases which affect the lower intestinal sections, for example the colon.

Pharmaceutical Composition

The inhibitors of the present invention, together with one or more conventional adjuvants, carriers, or diluents may be placed into the form of pharmaceutical compositions and unit dosages.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical composition and unit dosage forms may comprise conventional ingredients in conventional proportions, with or without additional active compounds or principles, and the unit dosage forms may contain any suitable effective amount of the active ingredients commensurate with the intended daily dosage range to be employed. The pharmaceutical composition may be employed as solids, such as tablets or filled capsules, semisolids, powders, sustained release formulations, or liquids such as solutions, suspensions, emulsions, elixirs, or filled capsules for oral use; or in the form of suppositories for rectal administration; or in the form of sterile injectable solutions for parenteral uses. Formulations containing about one (1) milligram of active ingredient or, more broadly, about 0.01 to about one hundred (100) milligrams, per tablet, are accordingly suitable representative unit dosage forms.

The compound of the present invention may be formulated in a wide variety of oral administration dosage forms. The pharmaceutical compositions and dosage forms may comprise compounds of the present invention or pharmaceutically acceptable salts thereof as the active component. The pharmaceutically acceptable carriers may be either solid or liquid. Solid form preparations include powders, tablets, pulls, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid, which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch gelatin, tragacanth, methylcellulose sodium carboxymethylcellulose, a low melting wax, cocoa butter, and the like.

The term "preparation" is intended to include the formulation of the active compound with an encapsulating material as carrier, providing a capsule in which the active component, with or without carriers, is surrounded by a carrier, which is in association with it. Similarly, cachets and lozenges are included. Tablets, powders, capsules, pulls, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavours, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilising agents, and the like.

The compound of the present invention may be formulated for parenteral administration (e.g., by injection, for example bolus injection or continuous infusion) and may be presented in unit dose form in ampoules, pre-filled syringes small volume infusion or in multi-dose containers with an added preservative. The compositions may take such forms as suspensions, solutions, or emulsions in oily or aqueous vehicles, for example solutions in aqueous polyethylene glycol. Examples of oily or non-aqueous carriers, diluents solvents or vehicles include propylene glycol, polyethylene glycol, vegetable oils (e.g., olive oil, and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

Synthesis of the Lipopetide of the Invention

The present invention also relates to a method to obtain a compound of the invention, characterized in that the compound of formula (I) is synthesized using peptide solid phase synthesis techniques or liquid phase synthesis technique.

The "peptide solid phase synthesis techniques" means synthesis strategies which are well known by the skilled person in the art, and can be found in peptide synthesis dedicated books such as: Paul Lloyd-Williams, Fernando Albericio, Ernest Giralt, "Chemical Approaches to the Synthesis of Peptides and Proteins", CRC Press, 1997 or Houben-Weyl "Methods of Organic Chemistry, Synthesis of Peptides and Peptidomimetics", Vol E 22a, Vol E 22b, Vol E 22c, Vol E 22d., M. Goodmann Ed., Georg Thieme Verlag, 2002 or in the review article Ann M. Thayer "Making Peptides At Large Scale". Chemical & Engineering News May 30, 2011 Volume 89, Number 22 pp. 21-25.

The "liquid phase synthesis technique" is classical organic synthesis methods which are well known from the one skilled in the art.

For the production of peptide at large scale (between 10 grams and 2 tonnes), it could be preferred to use liquid phase synthesis technique.

Accordingly, in a specific embodiment the method to obtain a compound of the invention is characterized in that the compound of formula (I) is synthesized using liquid phase synthesis technique.

The synthesis of C12-Asn-GABA started with GABA (γ-Aminobutyric Acid) was performed following 7 different steps which are summarized in the scheme below:

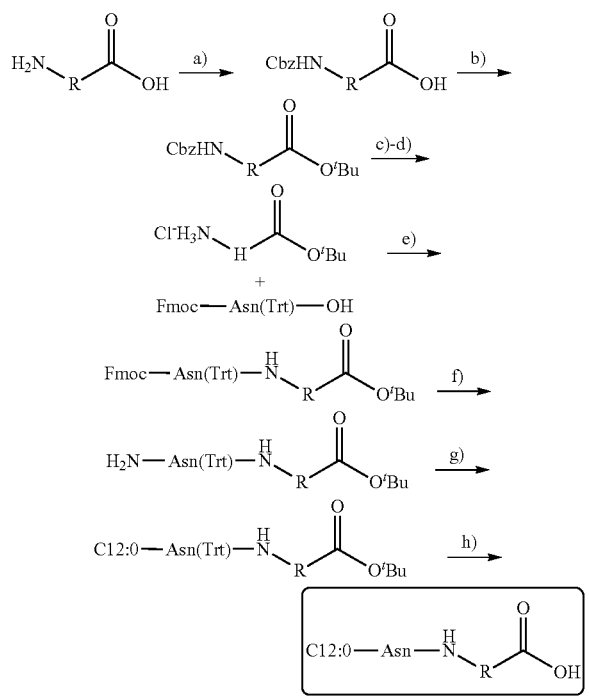

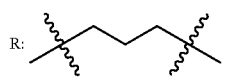

a) Cbz—Cl, NaOH, 0° C.;
b) DCC, DMAP, tBuOH, 36% to 50%;
c) H2, Pd/C, MeOH;
d) HCl, Et2O, 50% to 82%;
e) HBTU, HOBt, NMM, CH2Cl2, 90% to 97%;
f) Et2NH, CH2Cl2;
g) HBTU, HOBt, NMM, Lauric Acid CH2Cl2, 59% to 70%;
h) TFA, CH2Cl2, HPLC purification, 8% to 15%.

Abreviations:,
Cbz—Cl: Benzyl Chloroformate,
DCC: Dicyclohexylcarbodiimide,
DMAP: 4-(Dimethylamino)pyridine,
HBTU: N,N,N',N'-Tetramethyl-O-(1H-benzotriazol-1-yl) uroniumhexafluorophosphate,
HOBt: 1-Hydroxybenzotriazole hydrate,
NMM: 4-Methylmorpholine,
TFA: Trifluoroacetic Acid.

The details of preparation are described below.

1) CBz-GABA-OH: A solution of γ-aminobutyric acid (5.22 g, 50.6 mmol, 1 eq) in 2M NaOH solution (25 mL, 50 mmol, 1 eq) was cooled to 0° C. and treated with benzyl chloroformate (8.23 mL, 55.6 mmol, 1.15 eq), while pH is maintained around 10 by continuous addition of 3M NaOH solution. After 15 minutes, the reaction was allowed to stir at room temperature for 3 hours. After two extractions with Et$_2$O, the pH of the aqueous solution was adjusted to 1.5 by addition of 6M HCl solution. After having saturated with solid NaCl, the aqueous layer was extracted with EtOAc (3×50 mL). The combined organic layers were washed with brine (3×25 mL), dried over MgSO$_4$ and evaporated under vacuum. The oily residue was taken up with Et$_2$O and the solvent removed again to give a white solid of CBz-GABA-OH (11.3 g) used directly in the next step.

2) CBz-GABA-OtBu: To a solution of CBz-GABA-OH (11.3 g), tBuOH (14.5 mL, 152 mmol, 3 eq) and DMAP (620 mg, 5.1 mmol, 0.1 eq) in CH$_2$Cl$_2$, after cooling at 0° C., was added dicyclohexylcarbodiimide (12.52 g, 60.7 mmol, 1.2 eq). After one hour, the reaction was stirred vigorously overnight at room temperature. DCU was filtered and washed with EtOAc (2×5 mL). The filtrate was washed with 1M HCl solution (50 mL), and refiltrated. The aqueous layer was extracted with CH$_2$Cl$_2$ (3×50 mL). The combined organic layers were washed with brine (50 mL), 5% NaHCO$_3$ solution (50 mL) and brine (50 mL) again. The layer was dried over MgSO$_4$ and evaporated under vacuum. The crude was purified by column chromatography (pentane/AcOEt 90/10 to 70/30) to obtain CBz-GABA-OtBu (7.39 g, 50%). MS (ESI+) [M+Na]+ :316.17; [2M+Na]+ :609.00; MS (ESI−) [M]$^-$: 293.33.

3) GABA-OtBu. HCl: A solution of CBz-GABA-OtBu (2 g, 6.82 mmol, 1 eq) in MeOH (20 mL) was treated with Pd/C (10%, 200 mg, 10% w/w). After 6 hours, the catalyst was filtered over a Celite® pad. The solvent was carefully evaporated (caution, final product is volatile). 1M HCl solution (50 mL) was added. The aqueous layer was extracted with EtOAc (2×50 mL) and pH was adjusted to 10 by addition of NaOH pellets. The aqueous layer was extracted with EtOAc (3×50 mL). This last organic phase was washed with brine (2×25 mL), dried over MgSO$_4$ and carefully evaporated. The crude reaction mixture was dissolved in Et$_2$O (25 mL) and pH was adjusted to 1 by addition of 2M HCl solution in Et$_2$O. After 30 minutes of stirring, 676 mg GABA-OtBu. HCl (51% yield) was filtered and dried.

4) Fmoc-Asn(Trt)-GABA-OtBu: To a solution of Fmoc-Asn(Trt)-OH (328 mg, 0.55 mmol, 1.1 eq.) and GABA-OtBu. HCl (98 mg, 0.5 mmol, 1 eq.) in CH$_2$Cl$_2$ (4 mL) was added HBTU (176 mg, 0.75 mmol, 1.5 eq), HOBt (7 mg, 0.05 mmol, 0.1 eq) and N-methyl morpholine (176 μL, 1.6 mmol, 3.2 eq). The mixture was stirred overnight. The solvent was evaporated in presence of silica gel. The product was purified by column chromatography ($CH_2Cl_2$/MeOH 97.5/2.5) to obtain Fmoc-Asn(Trt)-GABA-OtBu (360 mg, 97%). MS (ESI+) $[M+H]^+$: 738.17; $[M+Na]^+$: 760.50; MS (ESI−) $[M-Fmoc]^-$: 514.58.

5) Asn(Trt)-GABA-OtBu: To a solution of Fmoc-Asn(Trt)-GABA-OtBu (350 mg, 0.47 mmol, 1 eq) in $CH_2Cl_2$ (1.35 mL) was added diethylamine (1.35 mL) and stirred for 2 h at room temperature. The resulting solution was concentrated in vacuum and used directly in the amine coupling step.

6) C12:0-Asn(Trt)-GABA-OtBu: To a solution of Asn(Trt)-GABA-OtBu (0.47 mmol, 1 eq.) and lauric acid (143 mg, 0.71 mmol, 1.5 eq.) in $CH_2Cl_2$ (4 mL) was added HBTU (194 mg, 0.83 mmol, 1.75 eq), HOBt (6 mg, 0.04 mmol, 0.1 eq) and N-methyl morpholine (195 μL, 1.77 mmol, 3.75 eq). The mixture was stirred overnight. The solvent was evaporated in presence of silica gel. The product was purified by column chromatography (pentane/AcOEt 75/25 to 60/40) to obtain C12:0-Asn(Trt)-GABA-OtBu (235 mg, 71%). MS (ESI+) $[M+H]^+$: 698.25; $[M+Na]^+$: 720.50; MS (ESI−) $[M]^-$: 696.75.

7) C12:0-Asn-GABA-OH: To a solution of C12:0-Asn(Trt)-GABA-OtBu (235 mg, 0.33 mmol, 1 eq) in $CH_2Cl_2$ (0.5 mL) was added TFA (0.5 mL) and stirred for 3 h at room temperature. The resulting solution was concentrated in a vacuum. Traces of TFA were eliminated by coevaporation with acetonitrile (5×2 mL). The crude reaction mixture was stirred with diisopropyl ether (10 mL) and filtrated. The resulting white solid (102 mg) was purified by HPLC to give 11 mg (8.6%) of C12:0-Asn-GABA-OH. Analytical LC-MS Rt: 1.62 mn; RMN (500 MHz, MeOD): δ=4.64 (t, J=6.9 Hz, 1H); 3.20 (t, J=6.6 Hz, 2H); 2.67 (dd, J=6.0, 15.3 Hz, 1H); 2.58 (dd, J=7.3, 15.3 Hz, 1H); 2.30 (t, J=7.4 Hz, 2H); 2.22 (t, J=7.4 Hz, 2H); 1.76 (quint, J=7.0 Hz, 2H); 1.57 (sl, 2H); 1.27 (sl, 16H), 0.93-0.86 (t, J=6.4 Hz, 3H); HRMS $[M+H]^+$ calc: 400.2811 found: 400.2804.

All reactions requiring anhydrous conditions were conducted in flame dried glassware with magnetic stirring under an atmosphere of nitrogen unless otherwise mentioned. Anhydrous $CH_2Cl_2$ was obtained from the Innovative Technology PS-Micro solvent purification system. Other solvents and reagents were used as obtained from the suppliers (Aldrich, Alfa Aesar, Acros) unless otherwise noted. Reactions were monitored by TLC using plates precoated with silica gel 60 (Merck). Reaction components were visualized by using a 254 nm UV lamp and treatment with basic $KMnO_4$ solution. Column chromatography was performed by using silica gel 40-63 μm. ES-MS and High resolution mass data were obtained using the mass spectrometers Synapt G2-S (Waters) operated by the Laboratoire de Mesures Physiques of University Montpellier and were obtained by positive electrospray ionization methods. $^1H$ NMR spectra were obtained at 300 or 500 MHz on Bruker spectrometers. The spectra were recorded in MeOD. The $^1H$ NMR spectra are reported as follow: chemical shift in ppm [multiplicity, coupling constant(s) J in Hz, relative integral]. The multiplicities are defined as follow: br.=broad, m=multiplet, s=singlet, d=doublet, t=triplet, q=quadruplet, quint.=quintuplet or combinations thereof. $^{13}C$ NMR spectra were recorded in MeOD. LCMS analysis were carried out on a Waters Micromass with Alliance 2695 chain with a Chromolite HR C18 column (25×4.6 mm, Merck Inc) monitoring at 214 nm with positive mode for mass detection. Solvents for LCMS were water with 0.1% formic acid (solvent A) and acetonitrile with 0.1% formic acid (solvent B). Compounds were eluted at a flow rate of 3 mL/min by a linear gradient of 0% to 100% solvent B over 2.5 min, and finally 100% solvent B for 1 min before equilibrating the column back to 0% solvent B over 1 min.

LC-MS Purification: samples were prepared in DMSO. The LC/MS autopurification system consisted of a binary pump Waters 2525, an injector/fraction collector Waters 2676, coupled to a Waters Micromass ZQ spectrometer (electrospray ionization mode, ESI+). Purifications were carried out using a Luna® 5 m C18 100 Å, LC Column 100×21.2 mm, AXIA™ Packed. A flow rate of 20 mL/min and a gradient of 40-60% B over 10 min were used. Eluent A: water with 0.1% TFA; eluent B: acetonitrile with 0.1% TFA. Positive ion electrospray mass spectra were acquired at a solvent flow rate of 204 μL/min. Nitrogen was used for both the nebulizing and drying gas. The data were obtained in a scan mode ranging from 100 to 1000 m/z in 0.1 s intervals; 10 scans were summed up to get the final spectrum. Collection control trigger is set on single protonated ion with a MIT (minimum intensity threshold) of 7.105.

The invention is further illustrated by the following figures and examples. However, these examples and figures should not be interpreted in any way as limiting the scope of the present invention.

FIGURES

FIG. 1: Characterization of C14-Asparagine (C14-Asn-OH) by LC-HRMS. (A) Total Ion Chromatogram (TIC) of a lipidic extract of EcNwt pellet (up) and EcNΔclbA pellet (down). (B) High resolution mass spectrum obtained for the peak eluted at 15.33 min in both TIC (top) and simulation of mass spectrum with the formula $(C_{18}H_{34}N_2O_4)$—H. Same isotopic profile and a mass accuracy of 0.6 ppm were obtained. (C) High energy MS/MS spectrum acquired via HCD of the electrospray carboxylate anion $[M-H]^-$ from the LC peak eluted at 15.33 min.

FIG. 2: Characterization of C12-Asparagine-aminobutyric acid by LC-HRMS. (A) Extracted Ion Chromatogram (EIC) of a lipidic extract of EcNwt (up) and EcNΔclbA pellet (down) for m/z=398.2664. No signal was detected in the mutated strain. (B) High resolution mass spectrum obtained for the peak eluted at 12.96 min in the probiotic strain EIC (top) and simulation of mass spectrum with the formula $(C_{20}H_{37}N_3O_5)$—$H^-$. Same isotopic profile and a mass accuracy of 1.8 ppm were obtained. (C) High energy MS/MS spectrum acquired via HCD of the electrospray carboxylate anion [M−H]− from the LC peak eluted at 12.96 min. (D) Upper panel: chromatogram obtained for the three synthesized standards: C12-Asn-γ-aminobutyric acid (GABA), C12-Asn-β-aminobutyric acid (BABA) and C12-Asn-α-aminobutyric acid (AABA); lower panel: Chromatogram obtained for the lipid extract of EcNwt pellet.

Figure 3B:
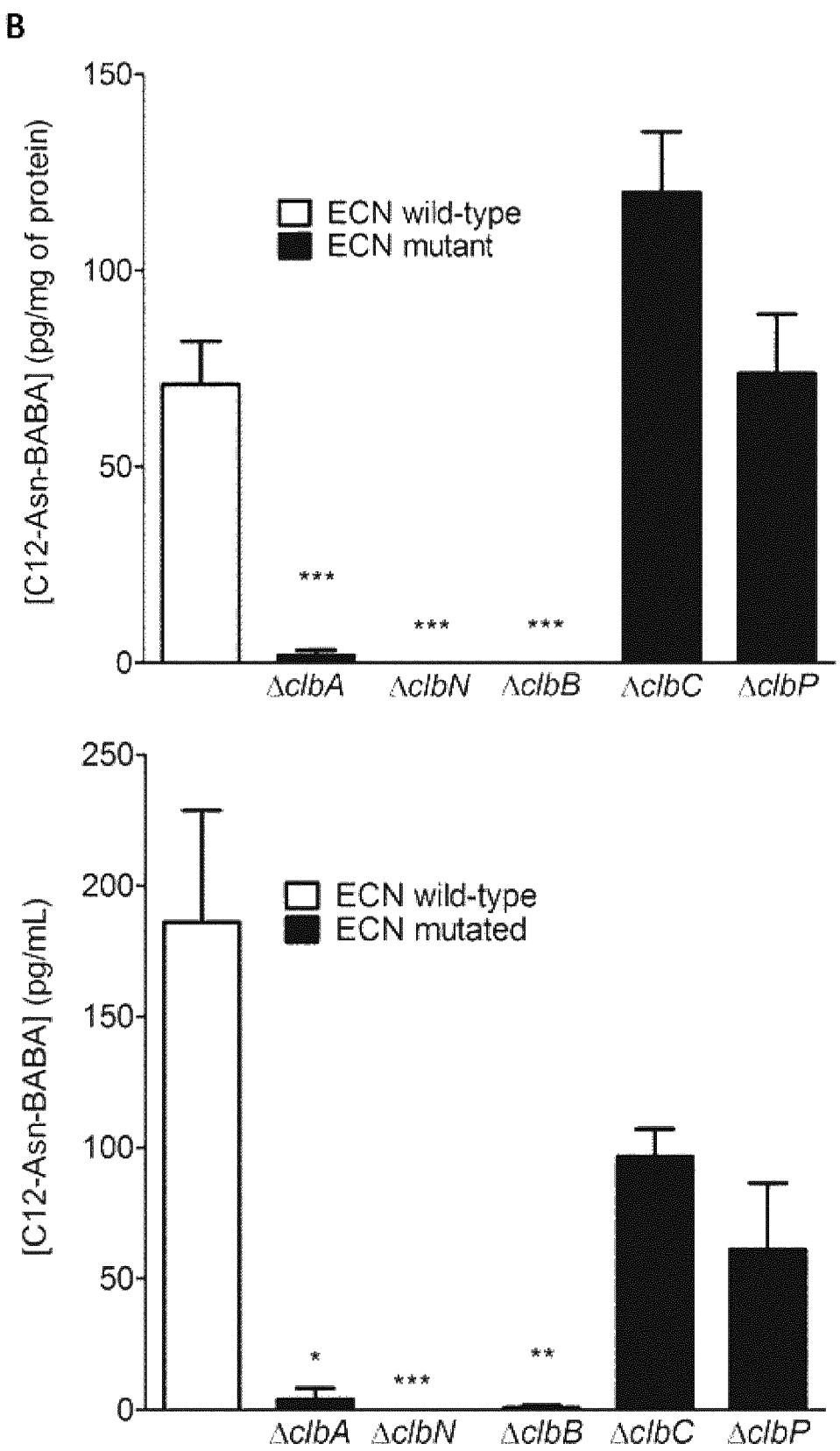

FIG. 3: quantification of C12-Asparagine-aminobutyric acid by LC-QQQ. (A) Quantification of C12-Asn-GABA in pellets (left panel) and supernatants (right panel) of wild type and mutated EcN. (B) Quantification of C12-Asn-BABA in pellets (left panel) and supernatants (right panel) of wild-type and mutated bacteria. Data are represented as mean±SEM of 2 experiments of 6 independent bacterial cultures per group. Statistical analysis was performed using Kruskal-Wallis analysis of variance and subsequent Dunn's post hoc test.*p<0.05, p<0.01, *p<0.001, significantly different from EcNwt.

FIG. 4: C12-Asn-GABA inhibits neuronal activation via the GABA B receptor. Amplitude of intracellular calcium mobilization (ΔF/F; right panel) in mouse sensory neurons and percentage of responding neurons (left panel) pretreated with increasing amounts of C12-Asn-GABA (black circle) or vehicle (HBSS; white circle) and treated with capsaicin (125 nM; A) or a mix of G protein coupled receptor agonists (histamine, serotonin and bradykinin 10 μM each; B). Data are represented as mean±SEM; n=4 independent experiments of 3 wells per condition and 30-80 neurons per well. Statistical analysis was performed using Kruskal-Wallis analysis of variance and subsequent Dunn's post hoc test. *p<0.05, **p<0.01 significantly different from capsaicin or GPCR mix. Percentage of responding neurons pretreated with increasing amounts of saclofen (black circle) or vehicle (HBSS; white circle) and treated with C12-Asn-GABA (10 μM) and capsaicin (125 nM; C) or a mix of G protein coupled receptor agonist (histamine, serotonin and bradykinin 10 μM each; D). Data are represented as mean±SEM; n=4 independent experiments of 3 wells per condition and 30-80 neurons per well. Statistical analysis was performed using Kruskal-Wallis analysis of variance and subsequent Dunn's post hoc test. *p<0.05, **p<0.01 significantly different from C12-Asn-GABA/Capsaicin or C12-Asn-GABA/GPCR mix.

FIG. 5: C12-Asn-GABA crosses the epithelial barrier without modifying epithelial cells physiology. Caco-2 cells were cultivated into transwell chambers. After treatment with C12-Asn-GABA (800 ng) at the apical side, C12-Asn-GABA was quantified inside the cells and both the apical and basolateral compartments by LC-MS/MS (A); data are represented as mean±SEM, n=3 experiments of 3 wells per condition. Extracted ion chromatogram at the exact mass of GABA (104.0702 m/z) with a mass accuracy of 5 ppm of the GABA commercial standard (GABA (Std.) and apical and basolateral compartments after loading or not Caco-2 cells with 800 ng of GABA at the apical site (B); representation of one well, n=3 experiments of 3 wells per condition. Paracellular permeability assessed by the passage of FITC-dextran loaded at the apical side (C) and CXCL8 secretion assessed by ELISA (D) were monitored after treatment of Caco-2 cells at the apical side with C12-Asn-GABA (10 μM); data are represented as mean±SEM, n=3 experiments of 3 wells per condition. Statistical analysis was performed using Kruskal-Wallis analysis of variance and subsequent Dunn's post hoc test.

FIG. 6: C12-Asn-GABA inhibits capsaicin-induced visceral hypersensitivity without altering Intestinal contraction. Mice received intracolonic administration of C12-Asn-GABA (10 μM; black symbols) or vehicle (40% ethanol; white symbols) and 30 minutes or 4 hours later colon (A) and blood (B) were harvested in order to quantify C12-Asn-GABA by LC-MS/MS. Data are expressed as mean±SEM, n=8 mice per group. Statistical analysis was performed using Kruskal-Wallis analysis of variance and subsequent Dunn's post hoc test. *p<0.001 significantly different from vehicle group. Mice received intracolonic administration of C12-Asn-GABA (10 μM; black symbols) or vehicle (40% ethanol; white symbols) and 30 minutes or 4 hours later an intracolonic administration of capsaicin (100 μg/mouse; square) or its vehicle (40% ethanol; circle). Fifteen minutes after capsaicin or vehicle treatment, visceromotor response (VMR) to increasing pressures of colorectal distension was performed. Data are expressed as mean±SEM, n=7-8 mice per group. Statistical analysis was performed using two-way Anova analysis of variance and subsequent Bonferroni post hoc test. *p<0.001 significantly different from Vehicle/Vehicle group. Ex vivo measurement of duodenal mechanical contraction frequency (B) and amplitude (C) in response to Krebs-Ringer solution (control; white bar), to DMSO 0.2% (vehicle; gray bar) or to C12-Asn-GABA (10 μM; black bar). Data are expressed as mean±SEM, n=5-6 per group. Statistical analysis was performed using Kruskal-Wallis analysis of variance and subsequent Dunn's post hoc test.

FIG. 7: C14-Asn-GABA inhibits neuronal activation by capsaicin. Amplitude of intracellular calcium mobilization (F/F; A) in mouse sensory neurons and percentage of responding neurons (B) pretreated with 10 μM of C14-Asn-GABA (black bar) or vehicle (HBSS; white bar) and treated with capsaicin (125 nM). Data are represented as mean±SEM; n=3 independent experiments of 3 wells per condition and 35-82 neurons per well. Statistical analysis was performed using Mann-Whitney U test. **p<0.01 significantly different from capsaicin.

Figure 8:
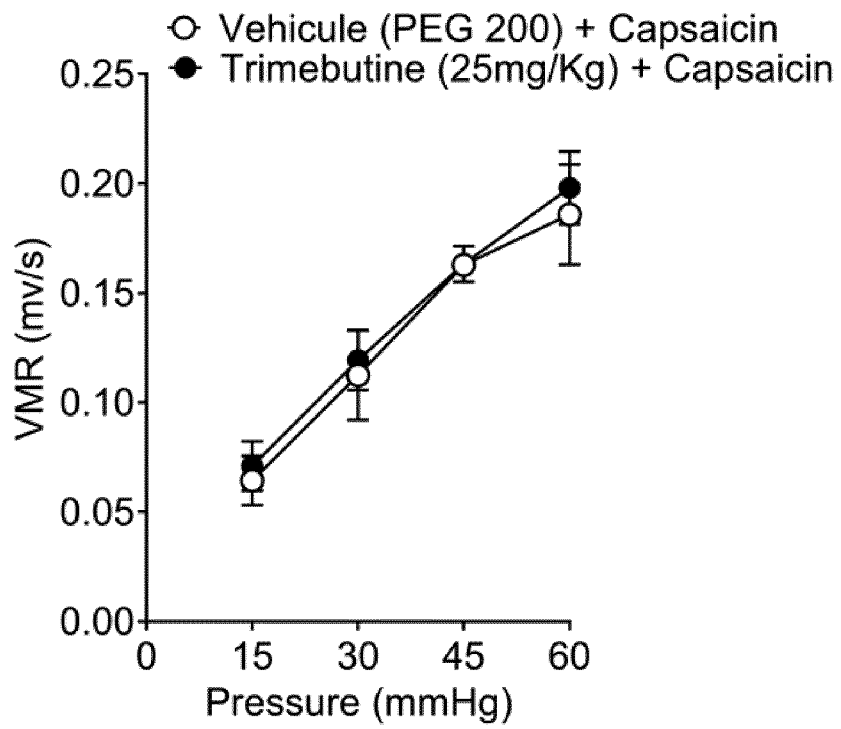

FIG. 8: Trimebutine maleate has no effect on capsaicin-induced visceral hypersensitivity. Mice received an oral treatment with vehicle (PEG200, white circle) or with trimebutine maleate (25 mg/kg, black circle) and 4 hours later an intracolonic administration of capsaicin (100 μg/mouse; black and white circle). Fifteen minutes after capsaicin, visceromotor response (VMR) to increasing pressures of colorectal distension was performed. Data are expressed as mean±SEM, n=7-8 mice per group.

Figure 9:
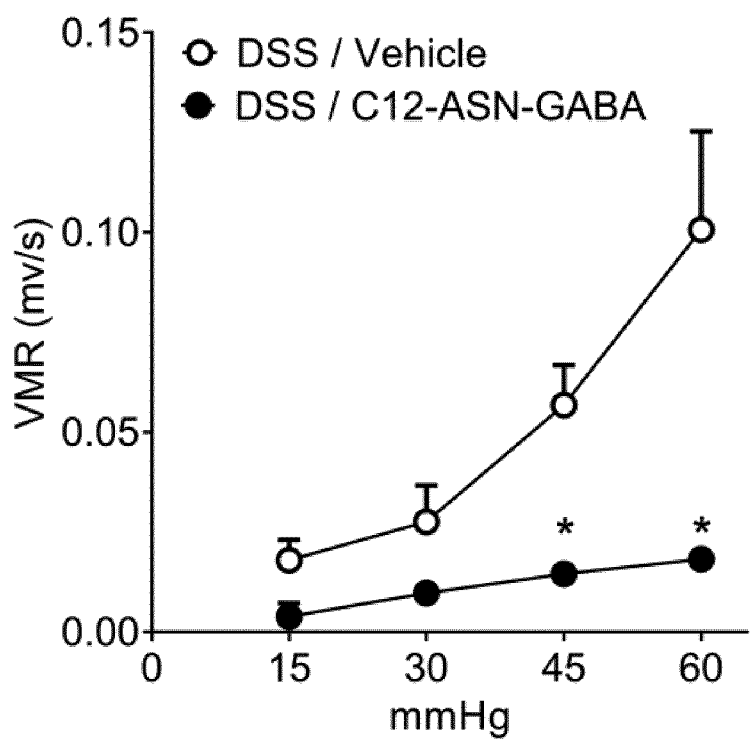

FIG. 9: C12-Asn-GABA Inhibits DSS-induced visceral hypersensitivity. Mice received DSS 3% in their drinking water for 5 days to induce colitis. At day 5, mice were intracolonically administrated with C12-Asn-GABA (10 μM; black circles) or vehicle (40% ethanol; white circles). Thirty minutes after intracolonic administration, visceromotor response (VMR) to increasing pressures of colorectal distension was performed. Data are expressed as mean±SEM, n=5 mice per group. Statistical analysis was performed using two-way Anova analysis of variance and subsequent Bonferroni post hoc test. ***p<0.001 significantly different from Vehicle/Vehicle group.

EXAMPLE 1

Material & Methods
Animals

Male C57B16 mice (6-8 weeks) were used to produce primary cultures of dorsal root ganglia (DRG) sensory neurons for calcium flux experiments, and to perform studies of colorectal distension and intestinal isotonic contraction. All procedures were approved by Institutional Animal Care Committees (CEEA 122).

Bacterial Strains.

E. coli MG1655, MG1655+BAC pks+, E. coli Nissle 1917 (EcN, Mutaflor, DSM 6601, serotype O6:K5:H1), the isogenic mutants EcNΔclbA, EcNΔclbN, EcNΔclbB, EcNΔclbC and EcNΔclbP were used in this study. Gene inactivation was engineered using the lambda red recombinase method[29] and deletions were confirmed by using flanking primers.

Extraction of Amino-Fatty Acids

E. coli were routinely cultured in 10 mL of Dulbecco's modified Eagle's medium (DMEM) for 8 h in a shaking incubator (250 rpm) at 37° C. Cell pellets and filtered culture supernatants were obtained in order to perform solid-phase extraction of amino-fatty acids by using HRX-50 mg 96-well plates (Macherey Nagel, Hoerd, France). Solvent was evaporated under $N_2$ and samples were resuspended in 10 µL MeOH for liquid chromatography/tandem mass spectrometry analysis[30].

Characterization of C12-Asn-Aminobutyric Acid

The characterization of C12-Asn-aminobutyric Acid was performed on a high performance liquid chromatograph (U3000, ThermoFisher Scientific, Waltham, Mass., USA) coupled on line to an Exactive high resolution mass spectrometer (ThermoFisher Scientific). MS analyses were performed in the negative FTMS mode at a resolution of 30 000 (at m/z 400) with the following source parameters: capillary temperature was 325° C., source heater temperature was 300° C., sheath gas flow rate was 30, auxiliary gas flow rate was 10 and source voltage was −2.9 kV. Samples were injected on a ZorBAX SB 120 C18 column (2.1×100 mm, 2.7 µm) (Agilent Technologies) maintained at 40° C. Solvent A was 0.1% formic acid in $H_2O$ and solvent B was 0.1% formic acid in acetonitrile at a flow rate of 350 µL/min. The linear gradient was as follows: 30% B at 0 min, 85% B at 15 min, 100% B at 15.1 min, 100% B at 16.5 min and 30% B at 16.7 min. The autosampler was set at 5° C. and the injection volume was 5 µL. The identification was performed using XCalibur software (Thermo Fisher Scientific).

Quantification of C12-Asn-GABA and C12-Asn-BABA

The quantification of C12-Asn-GABA and C12-Asn-BABA were performed on a high performance liquid chromatography (Agilent 1290 Infinity) coupled to a triple quadrupole mass spectrometer (G6460 Agilent). Chromatographic parameters were the same as used for the characterization. The HPLC system was coupled online to an Agilent 6460 triple quadrupole MS (Agilent Technologies) equipped with an electrospray ionization source. Electrospray ionization (ESI) was performed in negative ion mode. Source parameters used were as follows: source temperature was set at 325° C., nebulizer gas (nitrogen) flow rate was 10 L/min, sheath gas temperature was 400° C., sheath gas (nitrogen) flow rate was 12 L/min and the spray voltage was adjusted to −3.5 kV. Analyses were performed in Selected Reaction Monitoring detection mode (SRM) using nitrogen as collision gas. The specific transition was 398/295 corresponding to [M−H]-/[M-ABA-H]—. Ion optics and collision energy were optimized for C12-Asn-GABA and C12-Asn-BABA analysis. Peak detection, integration and quantitative analysis were done using Mass Hunter Quantitative analysis software (Agilent Technologies). Finally, the quantification of C12-Asn-GABA and C12-Asn-BABA were performed using a calibration curve calculated by the IS method. Six biological replicates were performed for each strain.

Cell Culture and Absorption/Permeability Experiments

Caco-2 cells were grown in Glutamax DMEM (Gibco, Invitrogen life technologies, Paisley, UK) supplemented with 10% heat-inactivated fetal bovine serum (FBS) (Gibco, Invitrogen life technologies, Paisley, UK), 1% nonessential amino acids and 1% antibiotics (100 U/ml penicillin and 100 mg/ml streptomycin (Gibco, Invitrogen life technologies, Grand Island, N.Y., USA) at 37° C. in a 5% C02 water-saturated atmosphere. Cells were seeded on Transwell inserts (Costar, Sigma-Aldrich, Saint-Quentin Fallavier, France) and absorption studies of C12-Asn-GABA and GABA were performed 16 days later. These compounds were quantified by LC-MS/MS in both apical and basolateral chambers as well as in cells. The effect of C12-Asn-GABA (1-100 µM) on paracellular permeability was also measured by mucosal-to-serosal flux of 4 kDa Fluorescein Isothiocyanate (FITC)-labelled dextran as previously described[31]. All experiments were performed in serum-free medium. CXCL8 concentration in apical and basolateral chambers was determined 24 hours after C12-Asn-GABA addition using a commercial enzyme-linked immunosorbent assay kit (BD biosciences, Erembodegen, Belgium) following manufacturer's recommendations[32].

Results

Identification of Amino-Fatty Acids Produced by EcN.

In order to characterize the lipids potentially implicated in probiotic properties of EcN, we performed a comparative lipidomic analysis without a priori by LC-HRMS of lipids extracted from the wild-type probiotic strain (EcNwt) and an isogenic mutant for clbA that has lost its probiotic activity (EcNΔclbA) in a model of colitis[23]. The total ion chromatograms (TIC) obtained were compared to characterize compounds with a relative concentration increased in EcNwt compared to EcNΔclbA. As the relative abundance of the peak eluted at 15.33 min represents more than 80% of the relative intensity in EcNwt and only 2.5% in EcNΔclbA, we focused our interest on this peak (FIG. 1A). With the exact mass obtained we determined a chemical composition of the molecule: $[C_{18}H34N2O4]$-H—. Then, the isotopic profile of the experimental mass spectrum obtained at 15.33 min was compared to the simulation spectrum generated from the formula. These two profiles were similar and the accuracy of the measure was 0.6 ppm (FIG. 1B) confirming the chemical composition. Finally, MS/MS analyses were performed. The spectrum showed ions at m/z 131, 114 and 96 that are specifics of the amino acid asparagine[25] and anion at m/z 226 corresponding to amyristoyl amid side chain[26]. Thus, with the fragmentation pattern we identified as expected the C14-Asparagine amino fatty acid which is the cleavage product of the precolibactin[18,21,22]. However, the extracted ion chromatogram of the ion at m/z 131 allowed us to identify additional molecules with an asparagine amino acid. Based on the mass accuracy of the mass spectrometer and the analysis of fragmentation mass spectra, we identified several amino fatty acids with different lengths of carbon chain as already published[21,22]. The characterization of other amino acids linked to the fatty acid chain was then performed by the use of the ion [M−H2O]—H—. We focused our interest on the ion at m/z 398.2664 eluted at 12.96 min. The extracted ion chromatograms showed that this molecule is present in EcNwt but not in the mutant EcNΔclbA (FIG. 2A). Mass accuracy obtained with LC-HRMS analysis allowed to identify its chemical formula, which was confirmed by the isotopic pattern of the simulation spectrum corresponding to the formula [C20H37N3O5]—H— (FIG. 2B). Fragments present in the fragmentation spectrum enabled us to determine that a butyric acid was linked to a C12-Asn amino fatty acid (FIG. 2C). Nevertheless, this characterization did not permit to determine the isomer of butyric acid linked to the fatty acid. In order to discriminate aminobutyric acid isomers linked to C12-Asn, we synthesized C12-Asn-α-aminobutyric (C12-Asn-AABA), C12-Asn-β-aminobutyric (C12-Asn-BABA) and C12-Asn-γ-aminobutyric (C12-Asn-GABA). The three synthesized isomers were analyzed on low-resolution mass spectrometry coupled on-line to a liquid chromatography. A 15 min separation method was developed for the separation of each isomer (FIG. 2D). The analysis of bacterial pellets showed the presence of only C12-Asn-GABA and C12-Asn-BABA (FIG. 2D).

C12-Asn-γ-Aminobutyric and C12-Asn-β-Aminobutyric Production by EcN is Dependent on the Pks Island.

*E. coli* K-12 MG1655 was transformed with the bacterial artificial chromosome (BAC) harboring the entire pks island (BAC pks+)[13]. Only the strain MG1655+BAC pks⁺ was shown to produce C12-Asn-BABA and C12-Asn-GABA demonstrating the role of the pks island in the production of these two compounds ( ). To further elucidate the role of the pks island in the synthesis of C12-Asn-GABA and C12-Asn-BABA, EcNΔclbA and additional isogenic mutants of the EcN strain were generated. These mutants (ΔclbA, ΔclbN, ΔclbB, ΔclbC and ΔclbP) were no more able to produce the genotoxin colibactin and to induce double-strand breaks in eukaryotic cells in contrast to the parental EcN strain. The lipid metabolite profiles were then characterized in EcN and the mutants, as well as in their culture supernatants. The inactivation of the clbA, gene coding for the PPTase induced a drastic decrease of both C12-Asn-GABA and C12-Asn-BABA in bacteria and culture supernatants (FIGS. 3B and 3C), confirming the relevance of this gene for the synthesis of these molecules. The clbN, clbB, clbC and clbP genes code for enzymes involved in the first steps and last steps of the biosynthesis of colibactin, namely the elongation and the cleavage of the colibactin pro-drug scaffold. Deletion of clbN completely abrogated the production and secretion of C12-Asn-GABA and C12-Asn-BABA in bacteria and their culture supernatants, evidencing the essential role of this gene in the production of these molecules. In a similar manner, clbB inactivation abolished the synthesis and secretion of C12-Asn-BABA and reduced significantly the synthesis and secretion of C12-Asn-GABA. On the contrary, mutation of clbC (a gene coding for a trans-acyl-transferase that catalyzes an additional round of polyketide extension, after ClbN and ClbB) did not induce significant changes in the concentration of any of the two molecules in both bacteria and supernatants. Likewise, the clbP deletion did not modify the synthesis and secretion pattern of any of these molecules demonstrating that C12-Asn-GABA and C12-Asn-BABA are not cleavage products. In contrast, and as expected, the concentration of the cleavage product, C14-Asn, was drastically decreased by clbP deletion. Thus, C12-Asn-GABA and C12-Asn-BABA are two new molecules dependent on at least three genes of the clb biosynthetic genes cluster, confirming the hypothesis that the pks island could mediate the formation of compounds with potential probiotic activity[23], in addition to molecules inducing DNA damage[13,27]. As among the aminobutyric acid isomers, the γ-aminobutyric (GABA) acid is the primary inhibitory neurotransmitter in the mammalian brain, we hypothesized that C12-Asn-GABA was responsible for the anti-nociceptive properties EcN.

C12-Asn-GABA Inhibits Neuronal Activation.

Figure 4A:
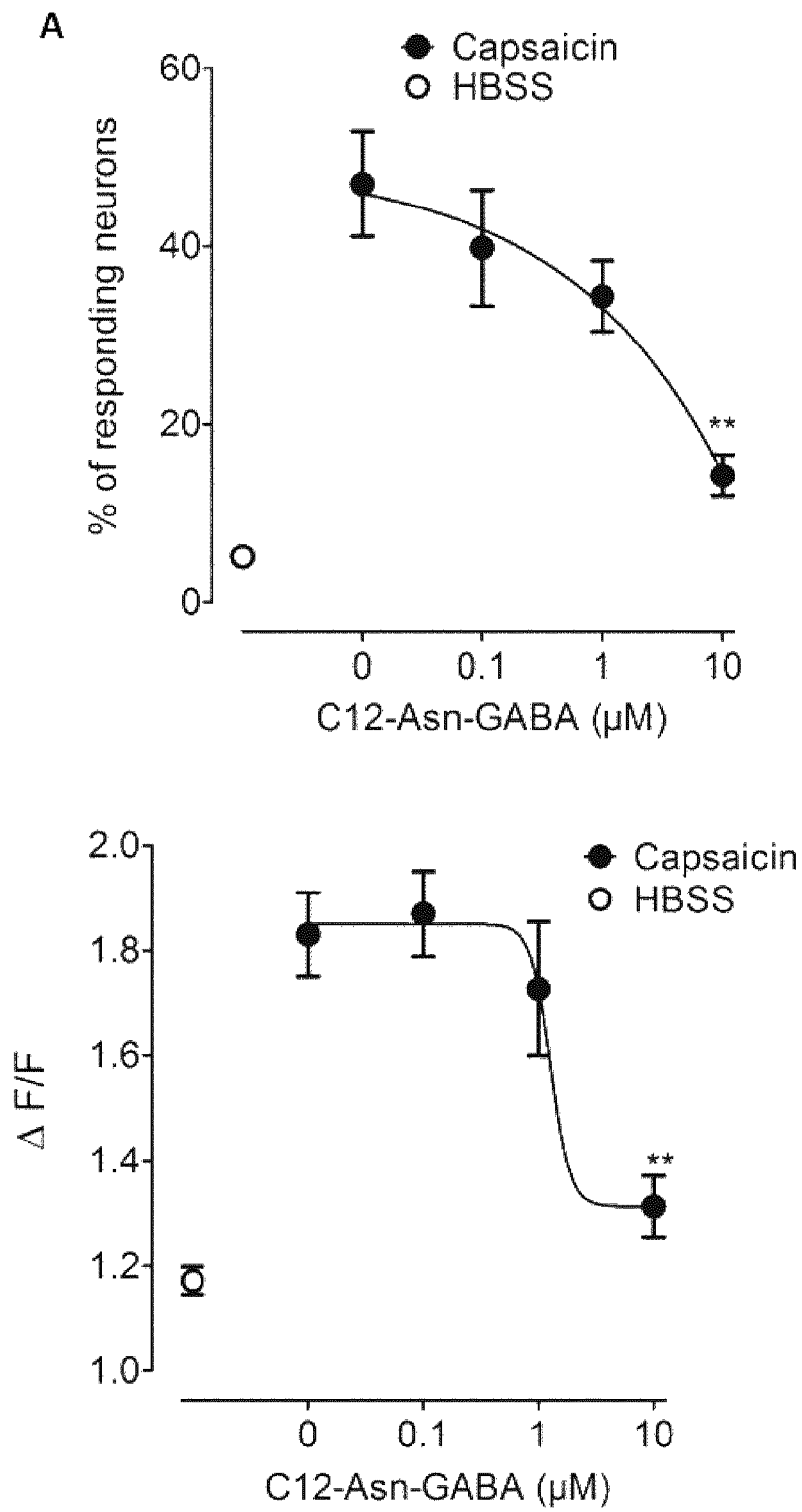
Figure 4B:
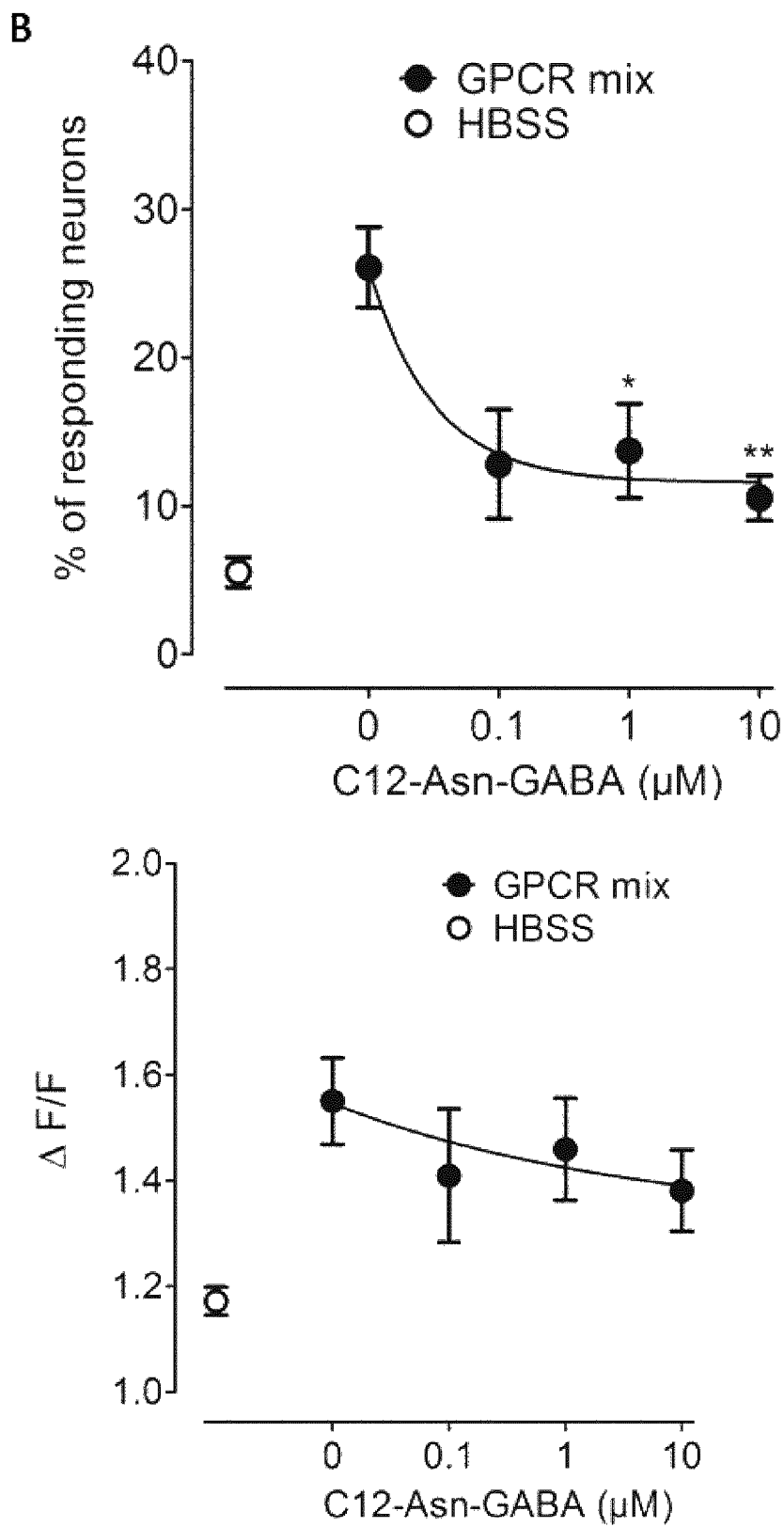

To determine whether C12-Asn-GABA or C12-Asn-BABA is capable of signaling to sensory nerves, calcium mobilization studies were performed on primary cultures of mouse dorsal root ganglia (DRG) neurons. None of the isomers (10 µM) induced calcium mobilization under basal (unstimulated) conditions. The same experiments were thereafter performed in neurons activated by either an agonist of the receptor calcium channel TRPV1 (capsaicin) or by a mix of agonists (histamine, serotonin and bradykinin) for G protein coupled receptors (GPCR) implicated in visceral hypersensitivity. Exposure of neurons to either capsaicin (125 nM) or the mix of GPCR agonists (histamine, bradykinin, serotonin, 10 µM each) induced an increase in calcium flux as shown by the higher % of responding neurons and amplitude of the response (ΔF/F) compared to the vehicle (FIG. 4A, 4B). The calcium flux increase induced by both nociceptive stimuli was prevented by C12-Asn-GABA pretreatment in a dose-dependent manner (FIG. 4A, 4B) whereas C12-Asn-BABA had no effect. Thus, C12-Asn-GABA does not induce calcium mobilization in sensory neurons but inhibits neuronal activation induced by pro-nociceptive stimuli. To investigate whether the inhibitory effect of C12-Asn-GABA was associated to the GABA residue, neurons were treated with saclofen (10, 50, and 100 µM), a competitive antagonist of the GABAB receptor. Treatment with saclofen abolished the inhibitory effect of C12-Asn-GABA against capsaicin and the mix of GPCR agonists in a dose-dependent-manner (FIG. 4C, 4D). Taken together, these results demonstrate that C12-Asn-GABA is capable of inhibiting calcium signaling in primary afferents via the GABAB receptor.

Figure 7A:
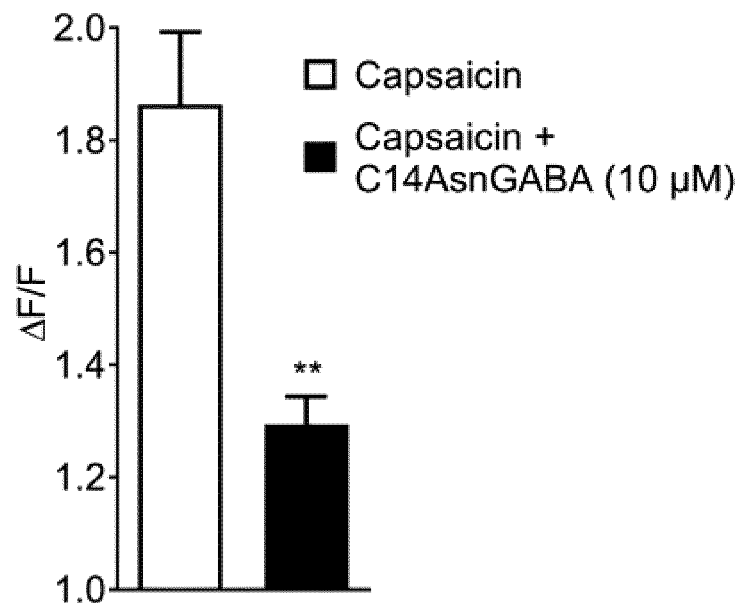
Figure 7B:
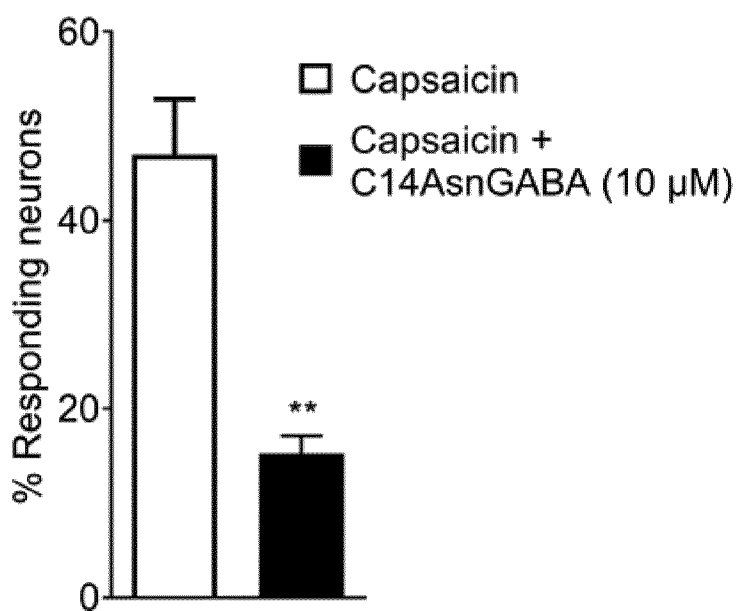

To determine whether the addition of 2 carbons on the fatty acid chain changed the inhibitory properties of the C12-Asn-GABA, cultures of sensory neurons were pretreated by the C14-Asn-GABA and 5 minutes later by the agonist of the receptor calcium channel TRPV1 (capsaicin). The calcium flux increase induced by capsaicin stimulus was prevented by C14-Asn-GABA pretreatment (FIG. 7A, 7B).

C12-Asn-GABA Crosses the Epithelial Barrier.

Figure 5A:
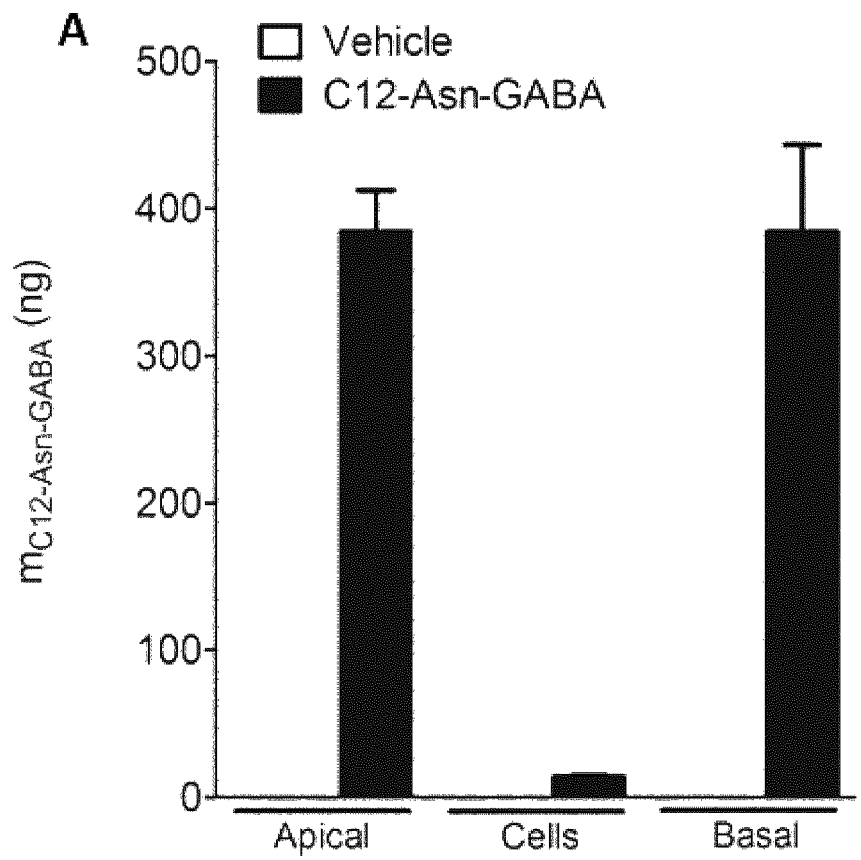
Figure 5C:
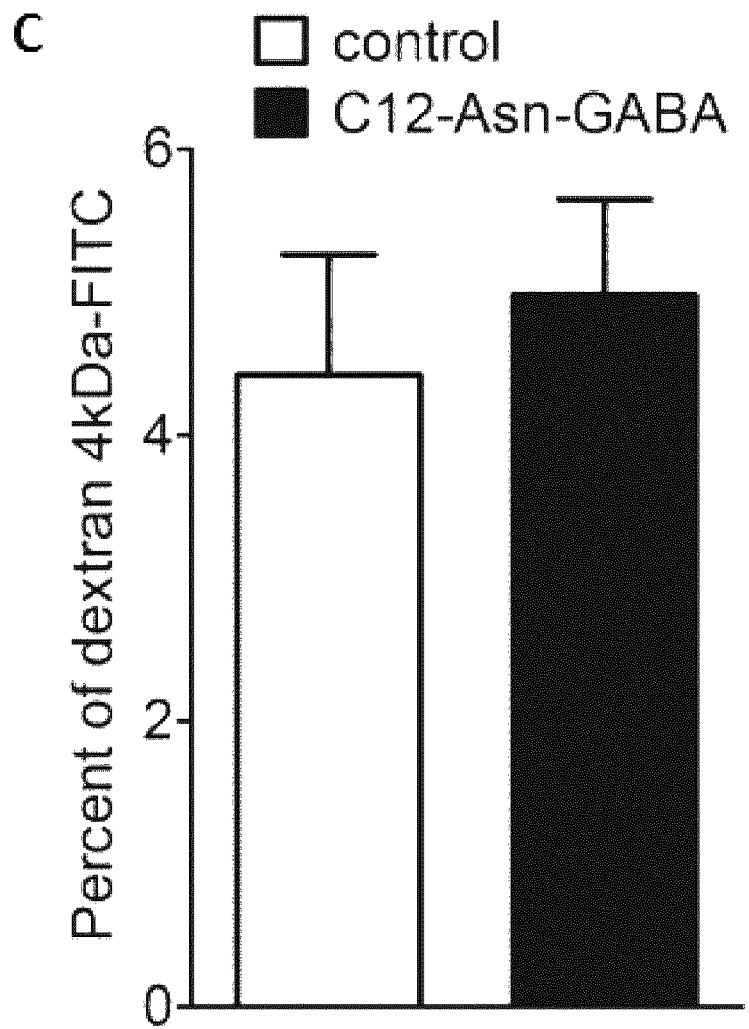

The initial barrier for any drug absorption is the intestinal epithelial cell wall. To evaluate whether C12-Asn-GABA is capable of crossing the epithelial barrier and then, stimulate GABA receptors on neurons[28], human epithelial cells monolayers (fully differentiated Caco-2 cells) were treated at the apical side by C12-Asn-GABA. Twenty-four hours after, LC-MS/MS quantification of this compound was performed in cells and in apical and basolateral side of transwell chambers. At the end of the incubation period, approximately 50% of C12-Asn-GABA added in the apical chamber (800 ng) was found in the basolateral chamber (FIG. 5A). Epithelial cells contained low levels of C12-Asn-GABA after 24 h of incubation. The transport of GABA alone across the cell monolayer was also assessed. For this purpose, commercial GABA was added in the apical chamber (800 ng) and, after 24 h, the presence of this molecule was quantified by LC-HRMS in basal and apical chambers (FIG. 5B). GABA was not detected in the basal chamber following the incubation period, showing that this molecule did not cross the intestinal epithelial monolayer. In conclusion, the C12-Asn-GABA is able to cross an epithelial cell monolayer. Thus, the addition of the C12-Asn by the bacteria to the GABA confers the capacity for this neuromediator to cross the intestinal epithelial barrier.

Figure 5D:
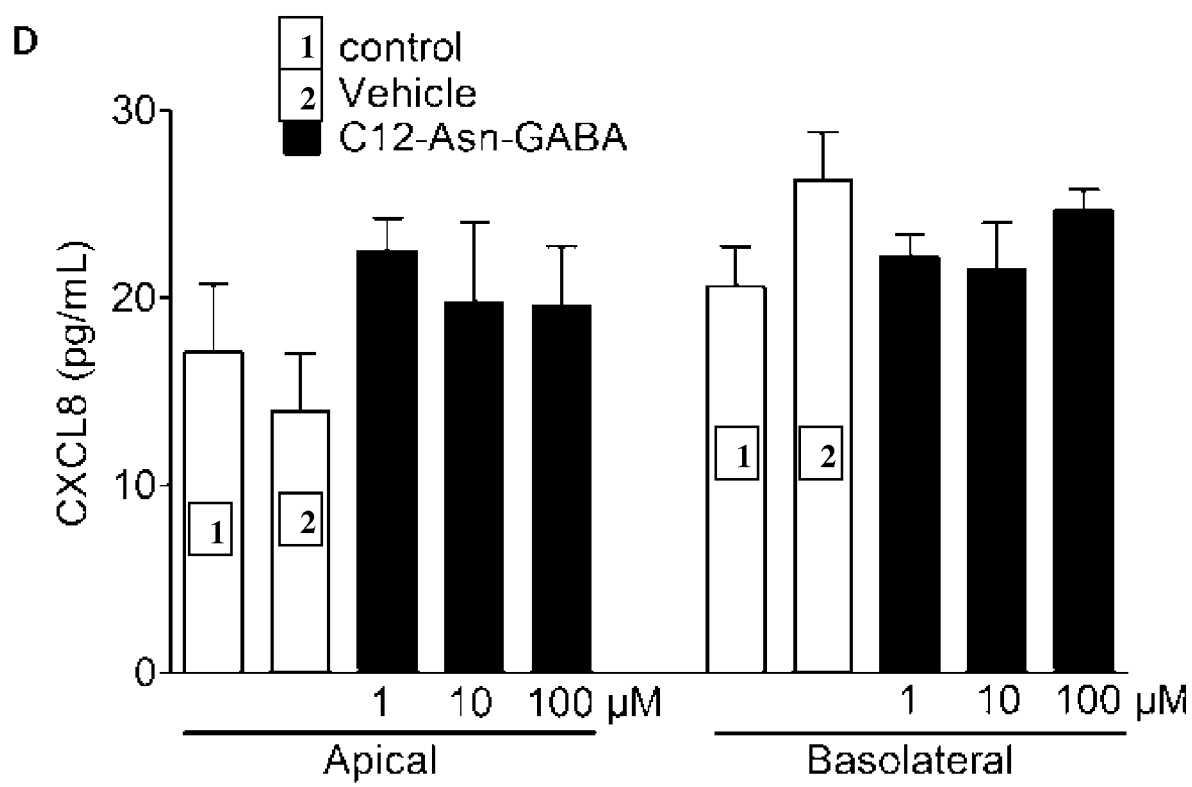

To assess the effect of C12-Asn-GABA on paracellular permeability, transport of dextran 4 kDa FITC across a Caco-2 cell monolayer was investigated. As shown in the FIG. 5C, the percentage of 4 kDa FITC traversing the cell monolayers after 24 h was not modified by C12-Asn-GABA (10 µM) treatment, evidencing that C12-Asn-GABA does not alter paracellular permeability. In parallel, the release of CXCL8 from Caco-2 cells into the medium, of both apical and basolateral sides of the transwell, was assessed by ELISA. None of the tested doses (1, 10, 100 µM) and neither the vehicle modified the secretion of CXCL8 by Caco2 cells (FIG. 5D). Thus, the addition of the C12-Asn by the bacteria to the GABA confers the capacity for this neuromediator to cross the intestinal epithelial barrier without altering paracellular permeability. We hypothesized that intracolonic administration of C12-Asn-GABA could mimic the luminal production of the analgesic amino-lipid by EcN and its diffusion across the epithelial barrier.

Intracolonic Administration of C12-Asn-GABA Inhibits Capsaicin-Induced Visceral Hypersensitivity without Altering Intestinal Contraction.

Figure 6C:
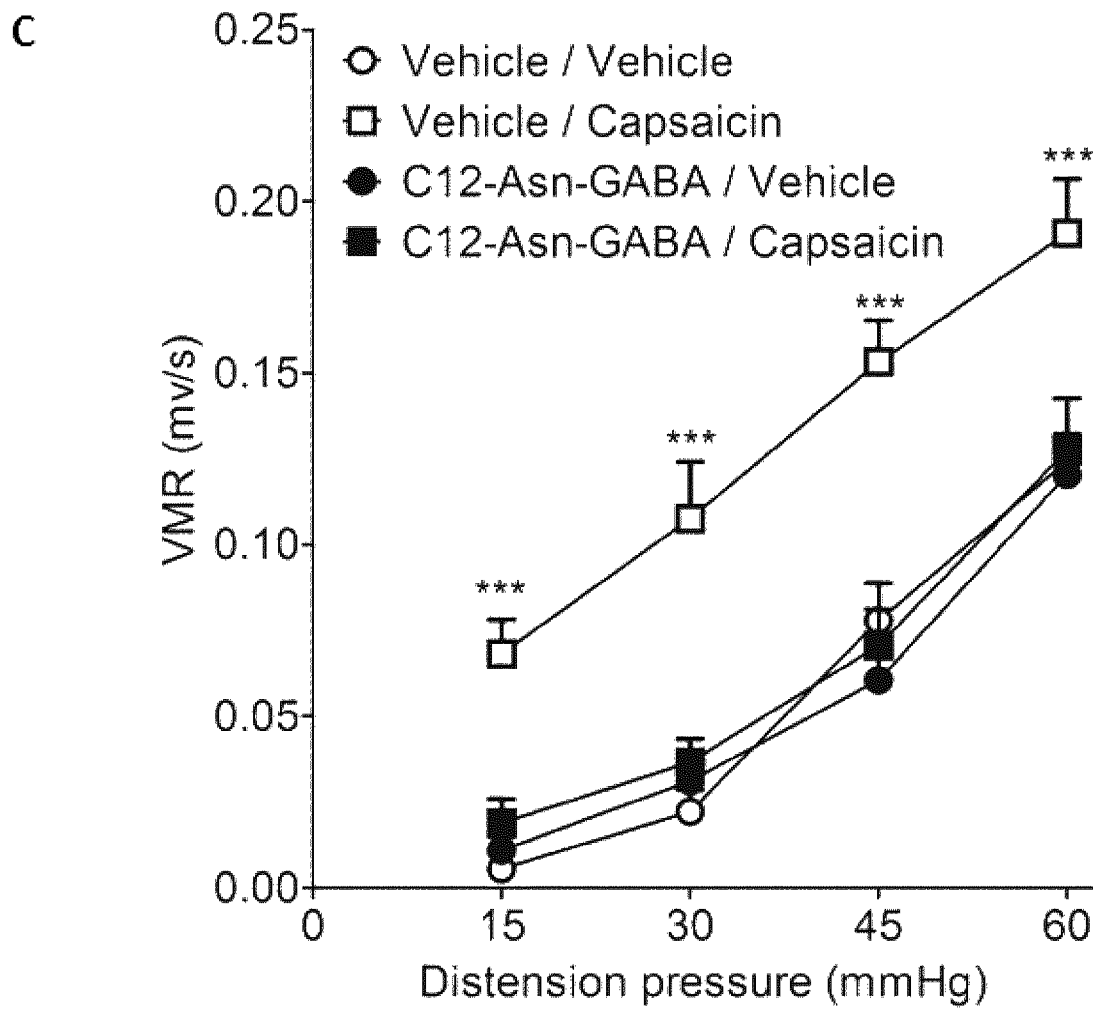

In a first set of experiment, we assessed the ability of the C12-Asn-GABA to cross the epithelial barrier, in vivo. Intracolonic administration of C12-Asn-GABA in mouse increased the concentration of this compound in the colonic tissue and in the blood (FIG. 6A, 6B). Based on its inhibitory effect on calcium mobilization in sensory neurons and on its capacity to cross the epithelial barrier in vivo, we evaluate the analgesic potency of this C12-Asn-GABA. The impact of C12-Asn-GABA on visceral hypersensitivity was assessed by measuring the visceromotor responses (VMR) to colorectal distension (CRD). VMR recordings were initiated 15 min after intracolonic administration of either capsaicin (100 µg/animal; 100 µL) or the vehicle (EtOH 40%). Capsaicin evoked an increase ($p<0.05$) in VMR to CRD pressures of 15-60 mm Hg compared to vehicle (FIG. 6C). This increase was significantly prevented for all distension pressures in animals pretreated with a 100 µL intracolonic injection of C12-Asn-GABA (10 µM), which showed similar VMR values to those obtained in the control group (vehicle/vehicle). C12-Asn-GABA administration in the absence of capsaicin did not modify visceral sensitivity in response to CRD (FIG. 6C). In contrast, trimebutine maleate, a drug classically used for the treatment of adult and adolescent patients with irritable bowel syndrome (IBS), has no effect on the hypersensitivity induced by capsaicin (FIG. 9).

IBS patients are characterized by diverse alterations of gut transit: diarrhea, constipation or mixed[1], thus a drug impairing bowel motility could limit its putative use in this pathology. We evaluated whether C12-Asn-GABA was capable of impairing duodenal motility. For this purpose, isotonic sensors were used to measure ex vivo mechanical contractions. Application of C12-Asn-GABA on ex vivo duodenal preparations impairs neither the frequency of contractions (FIG. 6D) nor the amplitude of intestinal contractions (FIG. 6E) compared to control and the vehicle.

The analgesic properties of the C12-Asn-GABA was assessed in a mouse colitis model. Dextran sulfate sodium (DSS) at 3% during 5 days was added in the drinking water in order to induce colitis. At day 5, the increase in VMR to CRD pressures of 15-60 mm Hg induced by DSS was significantly decreased for all distension pressures in animals treated with a 100 µL intracolonic injection of C12-Asn-GABA (10 µM).

CONCLUSION

We identified for the first time an amino fatty acid linked to GABA—the main inhibitory transmitter of the central nervous system-, exhibiting potent analgesic properties in visceral pain. Surprisingly, the synthesis of this C12-Asn-GABA requires three enzymes encoded by a genomic island, named pks, which carries the cluster of genes that enables the synthesis of hybrid peptide polyketides and especially the genotoxin colibactin, a bona fide virulence factor and a putative carcinogenic agent. Our results illustrate how the colibactin NRPS-PKS biosynthetic pathway clearly represents a rich source of unusual assembly line enzymology coding for additional bioactive compounds distinct from colibactin. This study is the first step in the characterization of a larger family of bioactive lipopetides produced by the gut microbiota. The addition of the C12-Asn confers to GABA the capacity to diffuse across the epithelial barrier and subsequently to act on sensory neurons. Interestingly, C12-Asn-GABA does not modify the physiology of the intestinal epithelium or the intestinal motility, leading to potentially fewer side effects than the prototypical analgesics such as morphine. Thus, C12-Asn-GABA may represent a very promising therapeutic agent for the management of visceral pain.

REFERENCES

Throughout this application, various references describe the state of the art to which this invention pertains. The disclosures of these references are hereby incorporated by reference into the present disclosure.

1. Mearin, F. et al. Bowel Disorders. Gastroenterology (2016).
2. Camilleri, M. et al. Prospective study of motor, sensory, psychologic, and autonomic functions in patients with irritable bowel syndrome. Clin Gastroenterol Hepatol 6, 772-81 (2008).
3. Kuiken, S. D., Lindeboom, R., Tytgat, G. N. & Boeckxstaens, G. E. Relationship between symptoms and hypersensitivity to rectal distension in patients with irritable bowel syndrome. Aliment Pharmacol Ther 22, 157-64 (2005).
4. Posserud, I. et al. Altered rectal perception in irritable bowel syndrome is associated with symptom severity. Gastroenterology 133, 1113-23 (2007).
5. Camilleri, M. Pharmacological agents currently in clinical trials for disorders in neurogastroenterology. J Clin Invest 123, 4111-20 (2013).
6. Didari, T., Mozaffari, S., Nikfar, S. & Abdollahi, M. Effectiveness of probiotics in irritable bowel syndrome: Updated systematic review with meta-analysis. World J Gastroenterol 21, 3072-84 (2015).
7. Ford, A. C. et al. Efficacy of prebiotics, probiotics, and synbiotics in irritable bowel syndrome and chronic idiopathic constipation: systematic review and meta-analysis. Am J Gastroenterol 109, 1547-61; quiz 1546, 1562 (2014).
8. Hungin, A. P. et al. Systematic review: probiotics in the management of lower gastrointestinal symptoms in clinical practice—an evidence-based international guide. Aliment Pharmacol Ther 38, 864-86 (2013).
9. Moayyedi, P. et al. The efficacy of probiotics in the treatment of irritable bowel syndrome: a systematic review. Gut 59, 325-32 (2010).
10. Sonnenborn, U. & Schulze, J. The non-pathogenic Escherichia coli strain Nissle 1917—features of a versatile probiotic. Microbial Ecology in Health and Disease 21, 37 (2009).
11. Faghihi, A. H., Agah, S., Masoudi, M., Ghafoori, S. M. & Eshraghi, A. Efficacy of Probiotic Escherichia coli Nissle 1917 in Patients with Irritable Bowel Syndrome: a Double Blind Placebo-controlled Randomized Trial. Acta Med Indones 47, 201-8 (2015).
12. Kruis, W., Chrubasik, S., Boehm, S., Stange, C. & Schulze, J. A double-blind placebo-controlled trial to study therapeutic effects of probiotic Escherichia coli Nissle 1917 in subgroups of patients with irritable bowel syndrome. Int J Colorectal Dis 27, 467-74 (2012).
13. Nougayrede, J. P. et al. Escherichia coli induces DNA double-strand breaks in eukaryotic cells. Science 313, 848-51 (2006).
14. Li, Z. R. et al. Divergent biosynthesis yields a cytotoxic aminomalonate-containing precolibactin. Nat Chem Biol 12, 773-5 (2016).
15. Bode, H. B. The Microbes inside Us and the Race for Colibactin. Angew Chem Int Ed Engl 54, 10408-11 (2015).
16. Taieb, F., Petit, C., Nougayrede, J. P. & Oswald, E. The Enterobacterial Genotoxins: Cytolethal Distending Toxin and Colibactin. EcoSal Plus 7(2016).

17. Martin, P. et al. Interplay between siderophores and colibactin genotoxin biosynthetic pathways in *Escherichia coli*. PLoS Pathog 9, e1003437 (2013).
18. Bian, X. et al. In vivo evidence for a prodrug activation mechanism during colibactin maturation. Chembiochem 14, 1194-7 (2013).
19. Vizcaino, M. I. & Crawford, J. M. The colibactin warhead crosslinks DNA. Nat Chem 7, 411-7 (2015).
20. Brotherton, C. A., Wilson, M., Byrd, G. & Balskus, E. P. Isolation of a metabolite from the pks island provides insights into colibactin biosynthesis and activity. Org Lett 17, 1545-8 (2015).
21. Brotherton, C. A. & Balskus, E. P. A prodrug resistance mechanism is involved in colibactin biosynthesis and cytotoxicity. J Am Chem Soc 135, 3359-62 (2013).
22. Vizcaino, M. I., Engel, P., Trautman, E. & Crawford, J. M. Comparative metabolomics and structural characterizations illuminate colibactin pathway-dependent small molecules. J Am Chem Soc 136, 9244-7 (2014).
23. Olier, M. et al. Genotoxicity of *Escherichia coli* Nissle 1917 strain cannot be dissociated from its probiotic activity. Gut Microbes 3, 501-9 (2012).
24. Secher, T., Brehin, C. & Oswald, E. Early settlers: which *E. coli* strains do you not want at birth? Am J Physiol Gastrointest Liver Physiol 311, G123-9 (2016).
25. Barbier Saint Hilaire, P. et al. Mechanistic study of competitive releases of H2O, NH3 and CO2 from deprotonated aspartic and glutamic acids: Role of conformation. J Chromatogr B Analyt Technol Biomed Life Sci (2016).
26. Boukerche, T. T. et al. Atypical cleavage of protonated N-fatty acyl amino acids derived from aspartic acid evidenced by sequential MS3 experiments. Amino Acids (2016).
27. Cuevas-Ramos, G. et al. *Escherichia coli* induces DNA damage in vivo and triggers genomic instability in mammalian cells. Proc Natl Acad Sci USA 107, 11537-42 (2010).
28. Hanack, C. et al. GABA blocks pathological but not acute TRPV1 pain signals. Cell 160, 759-70 (2015).
29. Datsenko, K. A. & Wanner, B. L. One-step inactivation of chromosomal genes in *Escherichia coli* K-12 using PCR products. Proceedings of the National Academy of Sciences of the United States of America 97, 6640-6645 (2000).
30. Le Faouder, P. et al. LC-MS/MS method for rapid and concomitant quantification of pro-inflammatory and pro-resolving polyunsaturated fatty acid metabolites. J Chromatogr B Analyt Technol Biomed Life Sci 932, 123-33 (2013).
31. Jung, C. et al. *Yersinia pseudotuberculosis* disrupts intestinal barrier integrity through hematopoietic TLR-2 signaling. J Clin Invest 122, 2239-51 (2012).
32. Alnabhani, Z. et al. *Pseudomonas fluorescens* alters the intestinal barrier function by modulating IL-1beta expression through hematopoietic NOD2 signaling. Inflamm Bowel Dis 21, 543-55 (2015).

The invention claimed is:

1. A compound of Formula (I):

RC(O)-Xaa-Xbb-Y, Formula (I)

wherein
R is a C5-C19 linear or branched hydrocarbon chain selected from the group consisting of alkyl, alkene, and alkyne,
Xaa is asparagine or an equivalent polar and non-charged amino acid selected from the group consisting of serine, threonine and glutamine,
Xbb is $HNCH_2CH_2CH_2CO$, and
Y is —OH or $NH_2$,
and wherein Xbb is linked to Xaa through its amine functional group and wherein the RC(O) group of Formula (I) is at the N terminal side and the Y group of Formula (I) is a C terminal side,
or a pharmaceutical acceptable salt thereof.

2. The compound of claim 1, wherein R is a C5-C19 alkyl.
3. The compound of claim 2, wherein R is a C11 alkyl.
4. The compound of claim 1, wherein Xaa is asparagine.
5. The compound of claim 1, wherein Y is —OH.
6. The compound of claim 1, wherein the compound is:
$C_{11}C(O)$-Asn-gamma-aminobutyric acid

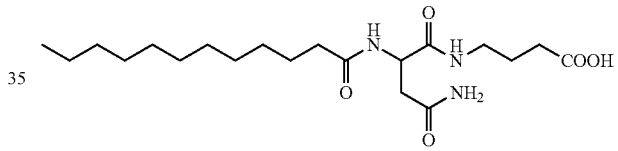

or a pharmaceutically acceptable salt thereof.

7. A method of treating Irritable Bowel Syndrome (IBS) or an Inflammatory Bowel Disease (IBD) in a subject in need thereof, comprising
administering to the subject a therapeutically effective amount of the compound of claim 1.

8. The method of claim 7 wherein the visceral pain disorder is Irritable Bowel Syndrome (IBS).

9. A pharmaceutical composition, comprising a compound according to claim 1, and one or more pharmaceutically acceptable excipients.

* * * * *